US011135249B2

(12) United States Patent
Itescu et al.

(10) Patent No.: US 11,135,249 B2
(45) Date of Patent: *Oct. 5, 2021

(54) METHODS FOR INCREASING OSTEOBLASTIC FUNCTION

(71) Applicant: Mesoblast, Inc., New York, NY (US)

(72) Inventors: Silviu Itescu, Melbourne (AU); Ravi Krishnan, Royston Park (AU)

(73) Assignee: MESOBLAST, INC, New York, NY (US)

( * ) Notice: Subject to any disclaimer, the term of this patent is extended or adjusted under 35 U.S.C. 154(b) by 101 days.

This patent is subject to a terminal disclaimer.

(21) Appl. No.: 16/460,734

(22) Filed: Jul. 2, 2019

(65) Prior Publication Data
US 2019/0343887 A1 Nov. 14, 2019

Related U.S. Application Data

(60) Division of application No. 15/485,637, filed on Apr. 12, 2017, now abandoned, which is a continuation of application No. 14/343,730, filed as application No. PCT/AU2012/001062 on Sep. 7, 2012, now Pat. No. 9,642,878.

(60) Provisional application No. 61/535,441, filed on Sep. 16, 2011, provisional application No. 61/532,772, filed on Sep. 9, 2011.

(51) Int. Cl.
A61K 35/28 (2015.01)
C12N 5/0775 (2010.01)
A61K 38/39 (2006.01)
A61P 19/08 (2006.01)
A61P 19/10 (2006.01)
A61K 35/12 (2015.01)

(52) U.S. Cl.
CPC .............. A61K 35/28 (2013.01); A61K 38/39 (2013.01); A61P 19/08 (2018.01); A61P 19/10 (2018.01); C12N 5/0663 (2013.01); A61K 2035/124 (2013.01)

(58) Field of Classification Search
CPC .................................................. C12N 5/0663
See application file for complete search history.

(56) References Cited

U.S. PATENT DOCUMENTS

| 5,226,914 | A | 7/1993 | Caplan |
| 5,837,539 | A | 11/1998 | Caplan |
| 6,087,113 | A | 6/2000 | Caplan |
| 7,732,126 | B2 | 6/2010 | Zhang et al. |
| 9,642,878 | B2 | 5/2017 | Itescu et al. |
| 2006/0193840 | A1 | 8/2006 | Gronthos et al. |
| 2008/0260694 | A1 | 10/2008 | Gronthos et al. |
| 2009/0155216 | A1 | 6/2009 | Yamada et al. |
| 2017/0274016 | A1 | 9/2017 | Itescu et al. |

FOREIGN PATENT DOCUMENTS

| CN | 101103101 | 1/2008 |
| JP | 2008-520185 | 6/2008 |
| JP | 2008-538495 | 10/2008 |
| WO | WO 2001/004268 | 1/2001 |
| WO | WO 2004/085630 | 10/2004 |
| WO | WO 2006/029347 A2 | 3/2006 |
| WO | WO 2006/032075 | 3/2006 |
| WO | WO 2006/032075 A1 | 3/2006 |
| WO | WO 2006/108229 A1 | 10/2006 |
| WO | WO 2006/134921 A1 | 12/2006 |
| WO | WO 2008/003042 A2 | 1/2008 |
| WO | WO 2009/018613 A1 | 2/2009 |
| WO | WO 2009/155656 A1 | 12/2009 |
| WO | WO 2011/078799 A1 | 6/2011 |
| WO | WO 2011/097242 A2 | 8/2011 |

OTHER PUBLICATIONS

Quarto et al. N Engl J Med, 2001,344:385-386.*
Nov. 1, 2012 Notification of Transmittal of the International Search Report and the Written Opinion of the International Searching Authority, or the Declaration, including an International Search Report and Written Opinion of the International Searching Authority in connection with PCT International Application No. PCT/AU2012/001062, filed Sep. 7, 2012.
Mar. 20, 2014 Notification Concerning Transmittal of International Preliminary Report on Patentability (Chapter I of the Patent Cooperation Treaty), including an International Preliminary Report on Patentability and Written Opinion of the International Searching Authority in connection with PCT International Application No. PCT/AU2012/001062, filed Sep. 7, 2012.
Aug. 15, 2014 Patent Examination Report No. 1 issued in connection with Australian Patent Application No. 2012307086.
May 3, 2016 Patent Examination Report No. 2 issued in connection with Australian Patent Application No. 2012307086.
Feb. 9, 2015 Extended European Search Report issued in connection with European Patent Application No. 1282995.8.
May 17, 2016 Official Action Summary issued in connection with Japanese Patent Application No. 2014-528798.
Mar. 14, 2016 Written Opinion of the Intellectual Property Office of Singapore issued in connection with Singaporean Patent Application No. 11201400218Y.
Jun. 30, 2015 Office Action issued in connection with U.S. Appl. No. 14/343,730.
Sep. 30, 2015 Communication in Response to Jun. 30, 2015 Office Action filed in connection with U.S. Appl. No. 14/343,730.
Nov. 12, 2015 Office Action issued in connection with U.S. Appl. No. 14/343,730.
Apr. 12, 2016 Amendment in Response to Nov. 12, 2015 Office Action filed in connection with U.S. Appl. No. 14/343,730.
May 25, 2016 Office Action issued in connection with U.S. Appl. No. 14/343,730.

(Continued)

Primary Examiner — Bin Shen
(74) Attorney, Agent, or Firm — John P. White

(57) ABSTRACT

This application provides methods for treating a human subject suffering from a bone fracture by administering to the subject a population of cells enriched from STRO-1+ multipotential cells and/or multipotential progeny of such cells.

12 Claims, 9 Drawing Sheets

(56) References Cited

OTHER PUBLICATIONS

Oct. 25, 2016 Amendment in Response to May 25, 2016 Office Action issued in connection with U.S. Appl. No. 14/343,730.
Dec. 19, 2016 Notice of Allowance issued in connection with U.S. Appl. No. 14/343,730.
Jun. 21, 2017 Amendment in Response to Apr. 21, 2017 Notice to Filed Corrected Application Papers filed in connection with U.S. Appl. No. 15/485,637.
Apr. 13, 2018 Office Action issued in connection with U.S. Appl. No. 15/485,637.
Jun. 12, 2018 Communication in Response to Apr. 13, 2018 Office Action filed in connection with U.S. Appl. No. 15/485,637.
Aug. 9, 2018 Office Action issued in connection with U.S. Appl. No. 15/485,637.
Dec. 6, 2018 Amendment in Response to Aug. 9, 2018 Office Action filed in connection with U.S. Appl. No. 15/485,637.
Jan. 4, 2019 Final Office Action issued in connection with U.S. Appl. No. 15/485,637.
Atkins et al. "RANKL Expression Is Related to the Differentiation State of Human Osteoblasts." Journal of Bone and Mineral Research, 18(6):1088-1098 (2003).
Bruder et al., "Bone Regeneration by Implantation of Purified, Culture-Expanded Human Mesenchymal Stem Cells", J. Orthop. Res., 16(2):155-162 (1998).
Granero-Molto et al., "Regenerative Effects of Transplanted Mesenchymal Stem Cells in Fracture Healing", Stem Cells, 27:1887-98 (2009).
Gronthos et al., "A Novel Monoclonal Antibody (STRO-3) Identifies an Isoform of Tissue Nonspecific Alkaline Phosphatase Expressed by Multipotent Bone Marrow Stromal Stem Cells", Stem Cells Dev., 16:953-63 (2007).
Horowitz et al., "Transplantability and therapeutic effects of bone marrow-derived mesenchymal cells in children with osteogenesis imperfecta", Nature Med., 5(3):309-13 (1999).
Rabin et al., "A new xenograft model of myeloma bone disease demonstrating the efficacy of human mesenchymal stem cells expressing osteoprotegerin by lentiviral gene transfer", Leukemia, 21:2181-91 (2007).
Undale et al., "Mesenchymal Stem Cells for Bone Repair and Metabolic Bone Diseases", Mayo Clin. Proc. 84(10):893-902 (2009).
Van den Holder et al., "Enrichment of osteogenic cell populations from rat bone marrow stroma", Biomaterials 28:249-55 (2007).
Notification of Transmittal of the International Search Report and the Written Opinion of the International Searching Authority, or the Declaration, including an International Search Report and Written Opinion of the International Searching Authority, dated Nov. 1, 2012 in connection with PCT International Application No. PCT/AU2012/001062, filed September 7, 2012.
Notification Concerning Transmittal of International Preliminary Report on Patentability (Chapter I of the Patent Cooperation Treaty), including an International Preliminary Report on Patentability and Written Opinion of the International Searching Authority, dated Mar. 20, 2014 by The International Bureau of WIPO in connection with PCT International Application No. PCT/AU2012/001062, filed Sep. 7, 2012.
Patent Examination Report No. 1, dated Aug. 15, 2014 in connection with Australian Patent Application No. 2012307086.
Patent Examination Report No. 2, dated May 3, 2016 in connection with Australian Patent Application No. 2012307086.
Extended European Search Report, dated Feb. 9, 2015 in connection with European Patent Application No. 1282995.8.
Official Action Summary, dated May 17, 2016 in connection with Japanese Patent Application No. 2014-528798.
Written Opinion of the Intellectual Property Office of Singapore, dated Mar. 14, 2016 in connection with Singaporean Patent Application No. 11201400218Y.
Office Action dated Jun. 30, 2015 in connection with U.S. Appl. No. 14/343,730.
Communication filed Sep. 30, 2015 in response to Office Action dated Jun. 30, 2015 in connection with U.S. Appl. No. 14/343,730.
Office Action dated Nov. 12, 2015 in connection with U.S. Appl. No. 14/343,730.
Amendment filed Apr. 12, 2016 in response to Office Action dated Nov. 12, 2015 in connection with U.S. Appl. No. 14/343,730.
Office Action dated May 25, 2016 in connection with U.S. Appl. No. 14/343,730.
Amendment filed Oct. 25, 2016 in response to Office Action dated May 25, 2016 in connection with U.S. Appl. No. 14/343,730.
Notice of Allowance dated Dec. 19, 2016 in connection with U.S. Appl. No. 14/343,730.
Apr. 13, 2018 Restriction Requirement in connection with U.S. Appl. No. 15/485,637, filed Apr. 12, 2017.
Jun. 12, 2018 Response to Apr. 13, 2018 Restriction Requirement in connection with U.S. Appl. No. 15/485,637, filed Apr. 12, 2017.
Office Action dated Aug. 9, 2018 in connection with U.S. Appl. No. 15/485,637, filed Apr. 12, 2017.
Amendment filed Dec. 6, 2018 in response to Office Action dated Aug. 9, 2018 in connection with U.S. Appl. No. 15/485,637, filed Apr. 12, 2017.
Jan. 4, 2019 Final Office Action in connection with U.S. Appl. No. 15/485,637, filed Apr. 12, 2017.
Jethva R, Otsuru S, Dominici M, Horwitz EM. Cell therapy for disorders of bone. Cytotherapy. 2009;11(1):3-17. doi: 10.1080/14653240902753477. PMID: 19191055.
Quarto R, Mastrogiacomo M, Cancedda R, Kutepov SM, Mukhachev V, Lavroukov A, Kon E, Marcacci M. Repair of large bone defects with the use of autologous bone marrow stromal cells. N Engl J Med. Feb. 1, 2001;344(5):385-6. doi: 10.1056/NEJM200102013440516. PMID: 11195802.
Seibel MJ. Biochemical markers of bone turnover: part I: biochemistry and variability. Clin Biochem Rev. Nov. 2005;26(4):97-122. PMID: 16648882; PMCID: PMC1320175.
Dominici M, Pritchard C, Garlits JE, Hofmann TJ, Persons DA, Horwitz EM. Hematopoietic cells and osteoblasts are derived from a common marrow progenitor after bone marrow transplantation. *Proc Natl Acad Sci U S A*. 2004;101(32):11761-11766. doi:10.1073/pnas.0404626101.

\* cited by examiner

Plasma Osteocalcin levels increased after each of 10/10 MPC injections by 2 weeks; maximal increase seen at lowest cell dose Percentage changes in osteocalcin levels following MPC treatment compared to baseline levels prior to treatment 4/5 animals show progressive increase in plasma total alkaline phosphatase over 6 months of MPC treatment (as measured by % increase in Area Under the Curve analysis between 18-24 weeks and 0-6 weeks)

EXHIBIT E

Percentage changes in total alkaline phosphatase levels following MPC treatment compared to baseline levels prior to treatment in individual animals

METHODS FOR INCREASING OSTEOBLASTIC FUNCTION

CROSS-REFERENCE TO RELATED APPLICATIONS

This application is divisional of U.S. Ser. No. 15/485,637, filed Apr. 12, 2017, now abandoned, which is a continuation of U.S. Ser. No. 14/343,730, filed Jul. 21, 2014, now U.S. Pat. No. 9,642,878, issued May 9, 2017, which is a § 371 national stage of PCT International Application No. PCT/AU2012/001062, filed Sep. 7, 2012, claiming the benefit of U.S. Provisional Application Nos. 61/535,441, filed Sep. 16, 2011 and 61/532,772, filed Sep. 9, 2011, the contents of each of which are hereby incorporated by reference in their entirety.

FIELD

The present disclosure relates to methods for increasing osteoblastic function in a subject in need thereof. These methods are useful for treating or preventing disorders mediated by osteoblastic function such as bone disorders and male infertility.

BACKGROUND

Osteoblasts are cells responsible for bone formation. These cells produce a matrix of osteoid, which is composed mainly of type a collagen, chondroitin sulfate and osteocalcin. Osteoblasts also mineralize this matrix, e.g., making use of zinc, copper and sodium.

Osteoblasts arise from osteoprogenitor cells located in the periosteum of bone and the bone marrow. Osteoprogenitors are immature progenitor cells that express the master regulatory transcription factor Cbfa1/Runx2. Osteoprogenitors are induced to differentiate into osteoblasts by various growth factors, including the bone morphogenetic proteins (BMPs), fibroblast growth factor (FGF), platelet-derived growth factor (PDGF) and transforming growth factor beta (TGF-β). Once osteoprogenitors start to differentiate into osteoblasts, they begin to express a range of genetic markers including Osterix, Coll, BSP, M-CSF, ALP, and osteocalcin, osteopontin, and osteonectin.

Osteocalcin (Bone Gla Protein: BGP) is a small vitamin K dependent calcium binding protein that was first discovered by Price et al. ((1976) Proc. Natl. Acad. Sci. 73:3373-5). This protein is synthesized primarily by osteoblasts and ondontoblasts and comprises 15 to 20% of the non-collagenous protein of bone. Posner et al. ((1980) J. Biol. Chem. 255:8685-91) have shown that mature osteocalcin contains three carboxyglutamic acid residues which are formed by post-translational vitamin K-dependent modification of glutamic acid residues. These residues have been further shown to be involved in the ability of osteocalcin to bind calcium ions (Brozovic et al. (1976) Brit. J Hacmatol. 32:9).

Osteocalcin is the principal extracellular matrix protein in bone required for normal bone mineralization. Normal bone mineral density is a result of hydroxyapatite crystals containing extracellular calcium and phosphate within a protein matrix. Calcium deposition within the protein matrix involves osteocalcin produced by osteoblasts. Phosphate deposition within the protein matrix involves Tissue Non-Specific Alkaline Phosphatase (TNAP) which regulates extracellular concentrations of inorganic pyrophosphate (ppi), a natural inhibitor of hyroxyapatite crystals. Mutations in the TNAP gene result in hypophosphatasia, characterized by elevated extracellular concentrations of inorganic pyrophosphate, poorly mineralized bones, spontaneous fractures It is now known that osteocalcin synergistically activates calcium sensing receptor 2 (CaR2) in the presence of calcium. Accordingly, alterations in osteocalcin expression or activity play a key role in disorders related to CaR2 function. For example, disorders in which the interaction of osteocalcin and CaR2 play a role include but are not limited to sperm motility and viability, and metabolic bone disorders such as osteoporosis.

Osteoporosis is a systemic skeletal disorder characterized by reduced bone mineral density and increased risk of fracture. The two major etiologies of osteoporosis are increased osteoclast activity which breaks down and reduced osteoblast activity. These features occur in the post-menopausal state and after chronic corticosteroid use, as well as in idiopathic instances. Most of the current treatment strategies for osteoporosis are focused on anti-resorptive agents, such as bisphosphonates, which inhibit the bone resorption activity of osteoclasts. Certain strategies, such as use of parathyroid hormone (PTH), focus on increasing osteoblast activity, which is measured using biomarkers for enhanced osteoblast activity such as osteocalcin and bone specific-alkaline phosphatase.

SUMMARY

The present inventors have found that systemic administration of multipotential cell preparations to non-human primates results in a dramatic increase in osteoblast activity, e.g., as indicated by increased levels of circulating osteocalcin and/or alkaline phosphatase in the primates. For example, the inventors have found that administering multipotential cell preparations systemically to the primates resulted in about a twenty-fold increase in plasma osteocalcin levels within 2 weeks of administration. The inventors have also found that administering multipotential cell preparations systemically to the primates resulted in about a detectable increase, e.g., a 5% or 10% increase in plasma alkaline phosphatase levels within 6 weeks of administration. This indicates that systemic administration of multipotential cell preparations will be useful in the treatment of diseases that are related to or caused by low levels of osteoblast activity and/or systemic osteocalin and/or alkaline phosphatase, such as metabolic bone disorders and low fertility in males.

Accordingly, the present disclosure provides a method of increasing osteoblastic function in a subject, the method comprising systemically administering to the subject a population of stem cells and/or progeny thereof and/or soluble factors derived therefrom.

In one example, the subject is suffering from a disorder associated with low osteoblast levels or activity and/or associated with low osteocalcin levels or activity.

The disorder may be a metabolic bone disorder or male infertility.

The metabolic bone disorder may be selected from the group consisting of osteomalacia, osteoporosis, osteopetrosis, Paget's disease and X-linked hypophosphatemic rickets, renal failure-associated osteodystrophy, marble bone disease, osteitis fibrosa cystica and glucocorticoid-induced bone loss.

In one example, the subject suffers from osteoporosis. In one example, the method prevents or reduces the risk of a fracture in the subject suffering from osteoporosis.

In one example, the subject suffers from a bone fracture. In one example, the method accelerates healing of the bone fracture and/or prevents delayed union of the bone fracture and/or prevents non-union of the bone fracture. In this regard, the subject can suffer from a metabolic bone disorder or male infertility. Alternatively, the subject can be a normal subject, i.e., not suffer from a metabolic bone disorder or male infertility. Thus, the subject can be any subject suffering from a fracture.

In one example, administration of the population of stem cells and/or progeny thereof and/or soluble factors derived therefrom results in an increase in plasma osteocalcin levels in the subject.

In one example, administration of the stem cells stimulates production of osteocalcin by osteoblasts in the subject.

In one example, administration of the population of stem cells and/or progeny thereof and/or soluble factors derived therefrom results in at least a five-fold, or at least a ten-fold, or at least a twenty-fold increase in plasma osteocalcin levels within 2 weeks (or 4 weeks or 6 weeks) of administration.

In one example, administration of the population of stem cells and/or progeny thereof and/or soluble factors derived therefrom results in an increase in plasma alkaline phosphatase levels in the subject.

In one example, administration of the stem cells stimulates production of alkaline phosphatase by osteoblasts in the subject.

In one example, administration of the population of stem cells and/or progeny thereof and/or soluble factors derived therefrom results in at least a five or ten or twenty or thirty or forty or fifty or sixty percent increase in plasma alkaline phosphatase levels within 6 weeks of administration compared to the level of plasma alkaline phosphatase prior to administration.

In one example the stem cells are multipotential cells. In another example the multipotential cells are STRO-1$^+$ cells. In yet another example the multipotential cells are STRO-1$^{bright}$ cells. In yet another example the STRO-1$^+$ cells co-express the TNAP marker.

In one example, a method as described herein comprises administering a population of cells enriched for STRO-1$^{bright}$ cells and/or progeny thereof and/or soluble factors derived therefrom.

In one example, a method as described herein comprises administering a population of cells enriched for STRO-1+ and tissue non-specific alkaline phosphatise$^+$ (TNAP)$^+$ cells and/or progeny thereof and/or soluble factors derived therefrom.

In one example, the population of stem cells and/or progeny and/or soluble factors is/are administered intravenously.

In one example, the population of stem cells and/or the progeny and/or the soluble factors are administered a plurality of times.

For example, the population of stem cells and/or the progeny and/or the soluble factors is/are administered once every four or more weeks.

For example, the population of stem cells and/or the progeny and/or the soluble factors is/are administered once every eight or more weeks.

For example, the population of stem cells and/or the progeny and/or the soluble factors is/are administered once every twelve or more weeks.

In one example, a method described herein according to any example comprises administering between $0.1 \times 10^6$ to $5 \times 10^6$ STRO-1$^+$ cells and/or progeny thereof per kg.

In one example, a method described herein according to any example comprises administering between $0.3 \times 10^6$ to $2 \times 10^6$ STRO-1$^+$ cells and/or progeny thereof per kg. For example, the method comprises administering about $1 \times 10^6$ or $2 \times 10^6$ STRO-1$^+$ cells and/or progeny thereof per kg.

In one example, a method described herein according to any example comprises administering a low dose of STRO-1$^+$ cells and/or progeny thereof. For example, low dose of STRO-1$^+$ cells and/or progeny thereof comprises between $0.1 \times 10^5$ and $0.5 \times 10^6$ STRO-1$^+$ cells and/or progeny thereof per kg. For example, the low dose of STRO-1$^+$ cells and/or progeny thereof comprises about $0.3 \times 10^6$ STRO-1$^+$ cells and/or progeny thereof per kg.

In one example, a method described herein according to any example comprises administering a high dose of STRO-1$^+$ cells and/or progeny thereof.

In one example, the population of stem cells and/or the progeny cells are autogeneic or allogeneic and/or the soluble factors can be derived from autogeneic or allogeneic cells. In one example, the population and/or the progeny are allogeneic and/or the soluble factors are from allogeneic cells.

In accordance with the above example, the method can additionally comprise obtaining the population of stem cells and/or progeny cells and/or soluble factors or can additionally comprise isolating the population of stem cells and/or progeny cells and/or soluble factors. In one example, isolation of the population of stem cells and/or progeny cells is based on expression of STRO-1 and/or TNAP.

In one example, the population of stem cells and/or progeny cells and/or soluble factors are obtained from the subject being treated. In another example, the population of stem cells and/or progeny cells and/or soluble factors are obtained from a different subject of the same species.

In one example, the population of stein cells and/or progeny cells have been culture expanded prior to administration and/or prior to obtaining the soluble factors.

In accordance with the above example, a method as described herein according to any example can additionally comprise culturing the population of stem cells and/or progeny cells.

In one example, the stem cells and/or progeny cells thereof and/or soluble factors derived therefrom are administered in the form of a composition comprising said stem cells and/or progeny cells thereof and/or soluble factors derived therefrom and a carrier and/or excipient.

In accordance with the above example, a method as described herein according to any example can additionally comprise formulating the population and/or progeny and/or soluble factors into a composition.

The present disclosure also provides a kit comprising a population of stem cells and/or progeny thereof and/or soluble factors derived therefrom packaged with instructions for use in a method described herein according to any example.

For example, the present disclosure provides a kit comprising a composition comprising the population and/or the progeny and/or the soluble factors packaged with product information indicating use of the composition in a method described herein according to any example.

The present disclosure also provides a method of treating or preventing a disorder associated with low osteoblast levels or activity in a subject, the method comprising administering to the subject a population of stem cells and/or progeny thereof and/or soluble factors derived therefrom.

In one example, the subject suffers from osteoporosis. In one example, the method prevents or reduces the risk of a fracture in the subject suffering from osteoporosis.

In one example, the subject suffers from a bone fracture. In one example, the method accelerates healing of the bone fracture and/or prevents delayed union of the bone fracture and/or prevents non-union of the bone fracture.

The present disclosure also provides a method for increasing osteocalcin levels (e.g., plasma osteocalcin levels) in a subject in need thereof, the method comprising administering (e.g., systemically administering) to the subject a population of stem cells as described herein and/or progeny thereof as described herein and/or soluble factors derived therefrom as described herein.

In one example, the cells or factors are administered in an amount sufficient to increase osteocalcin levels (e.g., plasma osteocalcin levels) in the subject.

In one example, the subject in need has reduced levels of osteocalcin, e.g., plasma osteocalcin, e.g., compared to the level in a normal and/or healthy population.

The present disclosure also provides a method for increasing alkaline phosphatase levels (e.g., plasma alkaline phosphatase levels) in a subject in need thereof, the method comprising administering (e.g., systemically administering) to the subject a population of stem cells as described herein and/or progeny thereof as described herein and/or soluble factors derived therefrom as described herein.

In one example, the cells or factors are administered in an amount sufficient to increase alkaline phosphatase levels (e.g., plasma alkaline phosphatase levels) in the subject.

In one example, the subject in need has reduced levels of alkaline phosphatase, e.g., plasma alkaline phosphatase, e.g., compared to the level in a normal and/or healthy population.

The present disclosure also provides a population of stem cells and/or progeny thereof and/or soluble factors derived therefrom for use in the treatment or prevention of male infertility or a metabolic bone disorder.

The present disclosure also provides use of a population of stem cells and/or progeny thereof and/or soluble factors derived therefrom in the manufacture of a medicament for treating or preventing male infertility or a metabolic bone disorder in a subject.

DETAILED DESCRIPTION

General Techniques and Selected Definitions

Figure 1:
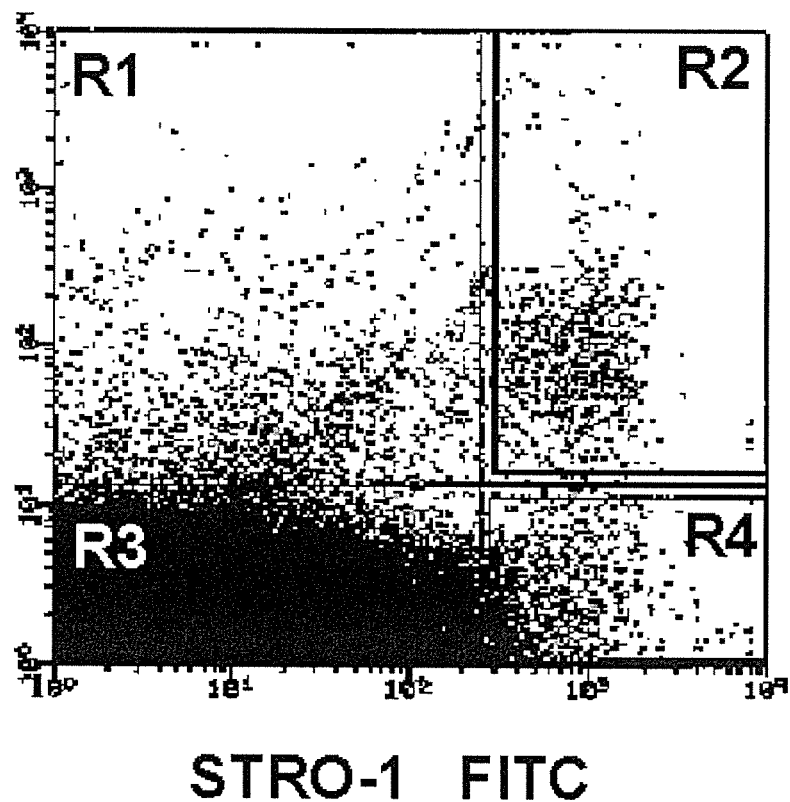
FIG. 1. Co-expression of TNAP (STRO-3) and the Mesenchymal Precursor Cell Marker, STRO-1$^{bright}$ by Adult Human bone marrow morphonuclear cells (BMMNC). Dual-color immunofluorescence and flow cytometry was performed by incubation of STRO-1 MACS-selected BMMNC and indirectly labeled with a goat anti-murine IgM antibody coupled to FITC (x axis), and STRO-3 mAb (murine IgG1) indirectly labeled with a goat anti-murine IgG coupled to PE (y axis). The dot plot histogram represents $5\times10^4$ events collected as listmode data. The vertical and horizontal lines were set to the reactivity levels of <1.0% mean fluorescence obtained with the isotype-matched control antibodies, IBS (IgG) and 1A6.12 (IgM) treated under the same conditions. The results demonstrate that a minor population of STRO-1$^{bright}$ cells co-expressed TNAP (upper right quadrant) while the remaining STRO-1+ cells failed to react with the STRO-3 mAb.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment or example described herein is to be applied mutatis mutandis to each and every other embodiment unless specifically stated otherwise.

Those skilled in the art will appreciate that the disclosure described herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific embodiments described herein, which are intended for the purpose of exemplification only. Functionally-equivalent products, compositions and methods are clearly within the scope of the disclosure, as described herein.

The present disclosure is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, pp 1-22; Atkinson et al, pp 35-81; Sproat et al, pp 83-115; and Wu et al, pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J. F. Ramalho Ortigao, "The Chemistry of Peptide Synthesis" In: Knowledge database of Access to Virtual Laboratory website (Interactiva. Germany); Sakakibara, D., Teichman, J., Lien, E. Land Fenichel, R. L. (1976). *Biochem. Biophys. Res. Commun.* 73 336-342; Merrifield, R. B. (1963). *J. Am. Chem. Soc.* 85, 2149-2154; Barany, G. and Merrifield, R. B. (1979) in The Peptides (Gross. E. and Meienhofer, J. eds.), vol. 2, pp. 1-284, Academic Press, New York. 12. Wünsch, E., ed. (1974) Synthese von Peptiden in Houben-Weyls Metoden der Organischen Chemie (Müler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) *Int. J. Peptide Protein Res.* 25, 449-474; Handbook of Experimental Immunology, Vols. I-IV (D. M. Weir and C. C. Blackwell, eds., 1986, Blackwell Scientific Publications); and Animal Cell Culture: Practical Approach, Third Edition (John R. W. Masters, ed., 2000), ISBN 0199637970, whole of text.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

As used herein the term "derived from" shall be taken to indicate that a specified integer may be obtained from a particular source albeit not necessarily directly from that source. In the context of soluble factors derived from stem cells and/or progeny cells thereof, this term shall be taken to mean one or more factors, e.g., proteins, peptides, carbohydrates, etc, produced during in vitro culturing of stem cells and/or progeny cells thereof.

As used herein, the term "osteoblastic function" will be understood to encompass the ability of an osteoblast to produce and/or secrete extracellular matrix, e.g., osteoid. Osteoid is an unmineralized bone matrix comprising type I collagen, chondroitin sulfate and osteocalcin. The term "osteoblastic function" additionally or alternatively means the ability of a cell to mineralize an extracellular matrix, e.g., osteoid. In one example, the term "osteoblastic function" will be understood to encompass increasing bone formation in a subject.

Increasing "osteoblastic function" in a subject can be achieved by increasing the ability of osteoblasts to produce and/or secrete extracellular matrix and/or to mineralize extracellular matrix and/or by increasing proliferation of osteoprogenitors and/or differentiation or osteoprogenitors into osteoblasts. For example, increasing osteoblastic function in a subject can be achieved by increasing the number of osteoblasts in a subject or in a bone thereof.

As used herein, the term "effective amount" shall be taken to mean a sufficient quantity of stem cells and/or progeny cells thereof and/or soluble factors derived therefrom to achieve a significant increase in osteoblastic function and/or osteoblast levels or activity and/or systemic osteocalcin levels and/or alkaline phosphatase levels in the subject. A significant increase in osteoblastic function and/or osteoblast levels or activity and/or systemic osteocalcin levels and/or alkaline phosphatase levels may be, for example, at least a two-fold increase, or at least a five-fold increase, or at least a ten-fold increase, at least a twenty-fold increase, or at least a twenty five-fold increase.

As used herein, the term "therapeutically effective amount" shall be taken to mean a sufficient quantity of stem cells and/or progeny cells thereof and/or soluble factors derived therefrom to treat a disorder associated with low osteoblast levels or activity.

As used herein, the term "prophylactically effective amount" shall be taken to mean a sufficient quantity of stem cells and/or progeny cells thereof and/or soluble factors derived therefrom to prevent or inhibit or delay the onset of a disorder associated with low osteoblast levels or activity As used herein, the term "low dose" shall be understood to mean an amount of stem cells and/or progeny thereof less than $1 \times 10^6$, yet still sufficient to be an "effective amount" as defined herein and/or a "therapeutically effective amount" and/or a "prophylactically effective amount" as defined herein. For example, a low dose comprises $0.5 \times 10^6$ or fewer cells, or $0.4 \times 10^6$ or fewer cells or $0.3 \times 10^6$ or fewer cells or $0.1 \times 10^6$ or fewer cells.

As used herein, the term "high dose" shall be understood to more than $1.5 \times 10^6$ cells/kg. For example, a dose comprises between about $1.5 \times 10^6$ and about $4 \times 10^6$ cells/kg. For example, a high dose comprises about $1.5 \times 10^6$ or about $2 \times 10^6$/kg.

As used herein, the term "treat" or "treatment" or "treating" shall be understood to mean administering a therapeutically effective amount of soluble factors and/or cells and reducing or inhibiting symptom(s) of a disorder associated with low osteoblast levels or activity such that the subject is no longer clinically diagnosed with the disorder.

As used herein, the term "prevent" or "preventing" or "prevention" shall be taken to mean administering a prophylactically effective amount of soluble factors and/or cells and stopping or hindering or delaying the development or progression of a disorder associated with low osteoblast levels or activity.

As used herein, the term "soluble factors" shall be taken to mean any molecule, e.g., protein, peptide, glycoprotein, glycopeptide, lipoprotein, lipopeptide, carbohydrate, etc. produced by stem cells and/or progeny thereof that are water soluble. Such soluble factors may be intracellular and/or secreted by a cell. Such soluble factors may be a complex mixture (e.g., supernatant) and/or a fraction thereof and/or may be a purified factor. In one example of the present disclosure soluble factors are or are contained within supernatant. Accordingly, any example herein directed to administration of one or more soluble factors shall be taken to apply mutatis mutandis to the administration of supernatant.

As used herein, the term "supernatant" refers to the non-cellular material produced following the in vitro culturing of stem cells and/or progeny thereof in a suitable medium, for example liquid medium. Typically, the supernatant is produced by culturing the cells in the medium under suitable conditions and time, followed by removing the cellular material by a process such as centrifugation. The supernatant may or may not have been subjected to further purification steps before administration. In one example, the supernatant comprises less than $10^5$, for example less than $10^4$, such as less than $10^3$, e.g., no live cells.

As used herein, the term "normal or healthy individual" shall be taken to mean a subject that does not have low osteoblastic activity as assessed by any method known in the art and/or described herein. In one example, a "normal or healthy individual" does not suffer from any of the symptoms of a disorder associated with low osteoblast levels or activity and/or does not suffer from a disorder associated with low osteoblast levels or activity.

Stem Cells or Progeny Cells, and Supernatant or One or More Soluble Factors Derived Therefrom As used herein, the term "stem cell" refers to self-renewing cells that are capable of giving rise to phenotypically and genotypically identical daughters as well as at least one other final cell type (e.g., terminally differentiated cells). The term "stem cells" includes totipotential, pluripotential and multipotential cells, as well as progenitor and/or precursor cells derived from the differentiation thereof. Thew stem cell may be an adult or embryonic stem cell or may be an induced pluripotent stem (iPS).

As used herein, the term "totipotent cell" or "totipotential cell" refers to a cell that is able to form a complete embryo (e.g., a blastocyst).

As used herein, the term "pluripotent cell" or "pluripotential cell" refers to a cell that has complete differentiation versatility, i.e., the capacity to grow into any of the mammalian body's approximately 260 cell types. A pluripotent cell can be self-renewing, and can remain dormant or quiescent within a tissue.

By "multipotential cell" or "multipotent cell" we mean a cell which is capable of giving rise to any of several mature cell types. As used herein, this phrase encompasses adult or embryonic stem cells and progenitor cells, such as mesenchymal precursor cells (MPC) and multipotential progeny of these cells. Unlike a pluripotent cell, a multipotent cell does not have the capacity to form all of the cell types.

As used herein, the term "progenitor cell" refers to a cell that is committed to differentiate into a specific type of cell or to form a specific type of tissue.

As used herein, the phrase "STRO-1$^+$ multipotential cells" shall be taken to mean STRO-1$^+$ and/or TNAP$^+$ progenitor cells capable of forming multipotential cell colonies.

STRO-1$^+$ multipotential cells are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum; and are capable of differentiating into germ lines such as mesoderm and/or endoderm and/or ectoderm. Thus, STRO-1$^+$ multipotential cells are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues. In one embodiment STRO-1$^+$ multipotential cells are non-hematopoietic progenitor cells which divide to yield daughter cells that are either stem cells or are precursor cells which in time will irreversibly differentiate to yield a phenotypic cell.

In one example, the STRO-1$^+$ cells are enriched from a sample obtained from a subject, e.g., a subject to be treated or a related subject or an unrelated subject (whether of the same species or different). The terms "enriched", "enrichment" or variations thereof are used herein to describe a population of cells in which the proportion of one particular cell type or the proportion of a number of particular cell types is increased when compared with an untreated population of the cells (e.g., cells in their native environment). In one example, a population enriched for STRO-1$^+$ cells comprises at least about 0.1% or 0.5% or 1% or 2% or 5% or 10/a or 15% or 20%$_0$ or 25% or 30% or 50% or 75% STRO-1$^+$ cells. In this regard, the term "population of cells enriched for STRO-1$^+$ cells" will be taken to provide explicit support for the term "population of cells comprising X % STRO-1$^+$ cells", wherein X % is a percentage as recited herein. The STRO-1$^+$ cells can, in some examples, form clonogenic colonies, e.g. CFU-F (fibroblasts) or a subset thereof (e.g., 50% or 60% or 70% or 70% or 90% or 95%) can have this activity.

In one example, the population of cells is enriched from a cell preparation comprising STRO-1$^+$ cells in a selectable form. In this regard, the term "selectable form" will be understood to mean that the cells express a marker (e.g., a cell surface marker) permitting selection of the STRO-1$^+$ cells. The marker can be STRO-1, but need not be. For example, as described and/or exemplified herein, cells (e.g., MPCs) expressing STRO-2 and/or STRO-3 (TNAP) and/or STRO-4 and/or VCAM-1 and/or CD146 and/or 3G5 also express STRO-1 (and can be STRO-1$^{bright}$). Accordingly, an indication that cells are STRO-1$^+$ does not mean that the cells are selected by STRO-1 expression. In one example, the cells are selected based on at least STRO-3 expression, e.g., they are STRO-3$^+$ (TNAP).

Reference to selection of a cell or population thereof does not require selection from a specific tissue source. As described herein STRO-1$^+$ cells can be selected from or isolated from or enriched from a large variety of sources. That said, in some examples, these terms provide support for selection from any tissue comprising STRO-1$^+$ cells (e.g., MPCs) or vascularized tissue or tissue comprising pericytes (e.g., STRO-1$^+$ pericytes) or any one or more of the tissues recited herein.

In one example, the cells used in the present disclosure express one or more markers individually or collectively selected from the group consisting of TNAP$^+$, VCAM-1$^+$, THY-1$^+$, STRO-2$^+$, STRO-4$^+$ (HSP-90β), CD45$^+$, CD146$^+$, 3G5$^+$ or any combination thereof.

By "individually" is meant that the disclosure encompasses the recited markers or groups of markers separately, and that, notwithstanding that individual markers or groups of markers may not be separately listed herein the accompanying claims may define such marker or groups of markers separately and divisibly from each other.

By "collectively" is meant that the disclosure encompasses any number or combination of the recited markers or groups of peptides, and that, notwithstanding that such numbers or combinations of markers or groups of markers may not be specifically listed herein the accompanying claims may define such combinations or sub-combinations separately and divisibly from any other combination of markers or groups of markers.

For example, the STRO-1 cells are STRO-1$^{bright}$ (syn. STRO-1$^{bri}$). In one example, the Stro-1$^{bri}$ cells are preferentially enriched relative to STRO-1$^{dim}$ or STRO-1$^{intermediate}$ cells.

For example, the STRO-1$^{bright}$ cells are additionally one or more of TNAP$^+$, VCAM-1$^+$, THY-1$^+$, STRO-2$^+$, STRO-4$^+$ (HSP-90β) and/or CD146$^+$. For example, the cells are selected for one or more of the foregoing markers and/or shown to express one or more of the foregoing markers. In this regard, a cell shown to express a marker need not be specifically tested, rather previously enriched or isolated cells can be tested and subsequently used, isolated or enriched cells can be reasonably assumed to also express the same marker.

In one example, the mesenchymal precursor cells are perivascular mesenchymal precursor cells as defined in WO 2004/85630. For example, the mesenchymal precursor cells express a marker of a perivascular cell, e.g., the cells are STRO-1 or STRO-1$^{bright}$ and/or 3G5$^+$ In one example, the cells are or were previously or are progeny of cells that were isolated from vascularized tissue or organs or parts thereof.

A cell that is referred to as being "positive" for a given marker it may express either a low (lo or dim) or a high (bright, bri) level of that marker depending on the degree to which the marker is present on the cell surface, where the terms relate to intensity of fluorescence or other marker used in the sorting process of the cells. The distinction of lo (or dim or dull) and bri will be understood in the context of the marker used on a particular cell population being sorted. A cell that is referred to as being "negative" for a given marker is not necessarily completely absent from that cell. This term means that the marker is expressed at a relatively very low level by that cell, and that it generates a very low signal when detectably labeled or is undetectable above background levels, e.g., levels detected suing an isotype control antibody.

The term "bright", when used herein, refers to a marker on a cell surface that generates a relatively high signal when detectably labeled. Whilst not wishing to be limited by theory, it is proposed that "bright" cells express more of the target marker protein (for example the antigen recognized by STRO-1) than other cells in the sample. For instance, STRO-1$^{bri}$ cells produce a greater fluorescent signal, when labeled with a FITC-conjugated STRO-1 antibody as determined by fluorescence activated cell sorting (FACS) analysis, than non-bright cells (STRO-1$^{dull/dim}$). In one example, "bright" cells constitute at least about 0.1% of the most brightly labeled bone marrow mononuclear cells contained in the starting sample. In other examples, "bright" cells constitute at least about 0.1%, at least about 0.5%, at least about 1%, at least about 1.5%, or at least about 2%, of the most brightly labeled bone marrow mononuclear cells contained in the starting sample. In an example, STRO-1$^{bright}$ cells have 2 log magnitude higher expression of STRO-1$^+$ surface expression relative to "background", namely cells that are STRO-1$^+$. By comparison, STRO-1$^{dim}$ and/or STRO-1$^{intermediate}$ cells have less than 2 log magnitude higher expression of STRO-1 surface expression, typically about 1 log or less than "background".

As used herein the term "TNAP" is intended to encompass all isoforms of tissue non-specific alkaline phosphatase. For example, the term encompasses the liver isoform (LAP), the bone isoform (BAP) and the kidney isoform (KAP). In one example, the TNAP is BAP. In one example, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

Furthermore, in one example, the STRO-1$^+$ cells are capable of giving rise to clonogenic CFU-F.

In one example, a significant proportion of the STRO-1$^+$ multipotential cells are capable of differentiation into at least two different germ lines. Non-limiting examples of the lineages to which the multipotential cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In another example, the STRO-1$^+$ cells are not capable of giving rise, upon culturing, to hematopoietic cells.

In one example, the cells are taken from the subject to be treated, cultured in vitro using standard techniques and used to obtain supernatant or soluble factors or expanded cells for administration to the subject as an autologous or allogeneic composition. In an alternative example, cells of one or more of the established human cell lines are used. In another useful example of the disclosure, cells of a non-human animal (or if the patient is not a human, from another species) are used.

The present disclosure also contemplates use of supernatant or soluble factors obtained or derived from STRO-1$^+$ cells and/or progeny cells thereof (the latter also being referred to as expanded cells) which are produced from in vitro culture. Expanded cells of the disclosure may a have a wide variety of phenotypes depending on the culture conditions (including the number and/or type of stimulatory factors in the culture medium), the number of passages and the like. In certain examples, the progeny cells are obtained after about 2, about 3, about 4, about 5, about 6, about 7, about 8, about 9, or about 10 passages from the parental population. However, the progeny cells may be obtained after any number of passages from the parental population.

The progeny cells may be obtained by culturing in any suitable medium. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells. In other words, a nutrient rich liquid prepared for bacterial culture is a medium. A powder mixture that when mixed with water or other liquid becomes suitable for cell culture may be termed a "powdered medium".

In an example, progeny cells useful for the methods of the disclosure are obtained by isolating TNAP$^+$ STRO-1$^+$ cells from bone marrow using magnetic beads labeled with the STRO-3 antibody, and then culture expanding the isolated cells (see Gronthos et al. *Blood* 85: 929-940, 1995 for an example of suitable culturing conditions).

In one example, such expanded cells (progeny) (for example, after at least 5 passages) can be TNAP$^+$, CC9$^+$, HLA class I$^+$, HLA class II$^+$, CD14$^+$, CD19$^+$, CD3$^+$, CD11a$^+$ c$^+$, CD31$^+$, CD86$^+$, CD34$^+$ and/or CD80$^+$. However, it is possible that under different culturing conditions to those described herein that the expression of different markers may vary. Also, whilst cells of these phenotypes may predominate in the expended cell population it does not mean that there is a minor proportion of the cells do not have this phenotype(s) (for example, a small percentage of the expanded cells may be CC9$^+$). In one example, expanded cells still have the capacity to differentiate into different cell types.

In one example, an expended cell population used to obtain supernatant or soluble factors, or cells per se, comprises cells wherein at least 25%, for example at least 50%, of the cells are CC9$^+$.

In another example, an expanded cell population used to obtain supernatant or soluble factors, or cells per se, comprises cells wherein at least 40%, for example at least 45%, of the cells are STRO-1$^+$.

In a further example, the expanded cells may express one or more markers collectively or individually selected from the group consisting of LFA-3, THY-1, VCAM-1, ICAM-1, PECAM-1, P-selectin, L-selectin, 3G5, CD49a/CD49b/CD29, CD49c/CD29, CD49d/CD29, CD 90, CD29, CD18, CD61, integrin beta 6-19, thrombomodulin, CD10, CD13, SCF, PDGF-R, EGF-R, IGFI-R, NGF-R, FGF-R, Leptin-R (STRO-2=Leptin-R), RANKL, STRO-4 (HSP-90p), STRO-1$^{bright}$ and CDI 46 or any combination of these markers.

In one example, the progeny cells are Multipotential Expanded STRO-1$^+$ Multipotential cells Progeny (MEMPs) as defined and/or described in WO 2006/032092. Methods for preparing enriched populations of STRO-1$^+$ multipotential cells from which progeny may be derived are described in WO 01/04268 and WO 2004/085630. In an in vitro context STRO-1$^+$ multipotential cells will rarely be present as an absolutely pure preparation and will generally be present with other cells that are tissue specific committed cells (TSCCs). WO 01/04268 refers to harvesting such cells from bone marrow at purity levels of about 0.1% to 90%. The population comprising MPCs from which progeny are derived may be directly harvested from a tissue source, or alternatively it may be a population that has already been expanded ex vivo.

For example, the progeny may be obtained from a harvested, unexpanded, population of substantially purified STRO-1$^+$ multipotential cells, comprising at least about 0.1, 1, 5, 10, 20, 30, 40, 50, 60, 70, 80 or 95% of total cells of the population in which they are present. This level may be achieved, for example, by selecting for cells that are positive for at least one marker individually or collectively selected from the group consisting of TNAP, STRO-4 (HSP-90p), STRO-1$^{bright}$, 3G5$^+$, VCAM-1, THY-1, CD146 and STRO-2.

MEMPS can be distinguished from freshly harvested STRO-1$^+$ multipotential cells in that they are positive for the marker STRO-1$^{bri}$ and negative for the marker Alkaline phosphatase (ALP). In contrast, freshly isolated STRO-1$^+$ multipotential cells are positive for both STRO-1$^+$ and ALP. In one example of the present disclosure, at least 15%, 20%, 30%, 40%, 50%, 60%, 70%, 80%, 90% or 95% of the administered cells have the phenotype STRO-1$^{bri}$, ALP$^+$. In a further example the MEMPS are positive for one or more of the markers Ki67, CD44 and/or CD49c/CD29, VLA-3, α3β1. In yet a further example the MEMPs do not exhibit TERT activity and/or are negative for the marker CD18.

The STRO-1$^+$ cell starting population may be derived from any one or more tissue types set out in WO 01/04268 or WO 2004/085630, namely bone marrow, dental pulp cells, adipose tissue and skin, or perhaps more broadly from adipose tissue, teeth, dental pulp, skin, liver, kidney, heart, retina, brain, hair follicles, intestine, lung, spleen, lymph node, thymus, pancreas, bone, ligament, bone marrow, tendon and skeletal muscle.

It will be understood that in performing methods described in the present disclosure, separation of cells carrying any given cell surface marker can be effected by a number of different methods, however, some exemplary methods rely upon binding a binding agent (e.g., an antibody or antigen binding fragment thereof) to the marker concerned followed by a separation of those that exhibit binding, being either high level binding, or low level binding or no binding. The most convenient binding agents are antibodies or antibody-based molecules, for example monoclonal antibodies or based on monoclonal antibodies (e.g., proteins comprising antigen binding fragments thereof) because of the specificity of these latter agents. Antibodies can be used for both steps, however other agents might also be used, thus ligands for these markers may also be employed to enrich for cells carrying them, or lacking them.

The antibodies or ligands may be attached to a solid support to allow for a crude separation. In some examples, the separation techniques maximize the retention of viability of the fraction to be collected. Various techniques of different efficacy may be employed to obtain relatively crude separations. The particular technique employed will depend upon efficiency of separation, associated cytotoxicity, ease and speed of performance, and necessity for sophisticated equipment and/or technical skill. Procedures for separation may include, but are not limited to, magnetic separation, using antibody-coated magnetic beads, affinity chromatography and "panning" with antibody attached to a solid matrix. Techniques providing accurate separation include but are not limited to FACS. Methods for performing FACS will be apparent to the skilled artisan.

Antibodies against each of the markers described herein are commercially available (e.g., monoclonal antibodies against STRO-1 are commercially available from R&D Systems, USA), available from ATCC or other depositary organization and/or can be produced using art recognized techniques.

In one example, the method for isolating STRO-1 cells comprises a first step being a solid phase sorting step utilizing for example magnetic activated cell sorting (MACS) recognizing high level expression of STRO-1. A second sorting step can then follow, should that be desired, to result in a higher level of precursor cell expression as described in patent specification WO 01/14268. This second sorting step might involve the use of two or more markers.

The method obtaining STRO-1$^+$ cells might also include the harvesting of a source of the cells before the first enrichment step using known techniques. Thus the tissue will be surgically removed. Cells comprising the source tissue will then be separated into a so called single cells suspension. This separation may be achieved by physical and or enzymatic means.

Once a suitable STRO-1+ cell population has been obtained, it may be cultured or expanded by any suitable means to obtain MEMPs.

In one example, the cells are taken from the subject to be treated, cultured in vitro using standard techniques and used to obtain supernatant or soluble factors or expanded cells for administration to the subject as an autologous or allogeneic composition. In an alternative example, cells of one or more of the established human cell lines are used to obtain the supernatant or soluble factors. In another useful example of the disclosure, cells of a non-human animal (or if the patient is not a human, from another species) are used to obtain supernatant or soluble factors.

Methods and uses of the present disclosure can be practiced using cells from any non-human animal species, including but not limited to non-human primate cells, ungulate, canine, feline, lagomorph, rodent, avian, and fish cells. Primate cells with which the disclosure may be performed include but are not limited to cells of chimpanzees, baboons, cynomolgus monkeys, and any other New or Old World monkeys. Ungulate cells with which the disclosure may be performed include but are not limited to cells of bovines, porcines, ovines, caprines, equines, buffalo and bison. Rodent cells with which the disclosure may be performed include but are not limited to mouse, rat, guinea pig, hamster and gerbil cells. Examples of lagomorph species with which the disclosure may be performed include domesticated rabbits, jack rabbits, hares, cottontails, snowshoe rabbits, and pikas. Chickens (Gal/us gal/us) are an example of an avian species with which the disclosure may be performed.

In one example, the cells are human cells.

Cells useful for the methods of the disclosure may be stored before use, or before obtaining the supernatant or soluble factors. Methods and protocols for preserving and storing of eukaryotic cells, and in particular mammalian cells, are known in the art (cf., for example, Pollard, J. W. and Walker, J. M. (1997) Basic Cell Culture Protocols, Second Edition, Humana Press, Totowa, N.J.; Freshney, R. I. (2000) Culture of Animal Cells, Fourth Edition, Wiley-Liss, Hoboken, N.J.). Any method maintaining the biological activity of the isolated stem cells such as mesenchymal stem/progenitor cells, or progeny thereof, may be utilized in connection with the present disclosure. In one example, the cells are maintained and stored by using cryo-preservation.

Genetically-Modified Cells

In one example, the stem cells and/or progeny cells thereof are genetically modified, e.g., to express and/or secrete a protein of interest. For example, the cells are engineered to express a protein useful in the treatment of a metabolic bone disorder or male infertility.

Methods for genetically modifying a cell will be apparent to the skilled artisan. For example, a nucleic acid that is to be expressed in a cell is operably-linked to a promoter for inducing expression in the cell. For example, the nucleic acid is linked to a promoter operable in a variety of cells of a subject, such as, for example, a viral promoter, e.g., a CMV promoter (e.g., a CMV-IE promoter) or a SV-40 promoter. Additional suitable promoters are known in the art and shall be taken to apply mutatis mutandis to the present example of the disclosure.

In one example, the nucleic acid is provided in the form of an expression construct. As used herein, the term "expression construct" refers to a nucleic acid that has the ability to confer expression on a nucleic acid (e.g. a reporter gene and/or a counter-selectable reporter gene) to which it is operably connected, in a cell. Within the context of the present disclosure, it is to be understood that an expression construct may comprise or be a plasmid, bacteriophage, phagemid, cosmid, virus sub-genomic or genomic fragment, or other nucleic acid capable of maintaining and/or replicating heterologous DNA in an expressible format.

Methods for the construction of a suitable expression construct for performance of the disclosure will be apparent to the skilled artisan and are described, for example, in Ausubel et al (In: Current Protocols in Molecular Biology. Wiley Interscience, ISBN 047 150338, 1987) or Sambrook et al (In: Molecular Cloning: Molecular Cloning: A Laboratory Manual, Cold Spring Harbor Laboratories, New York, Third Edition 2001). For example, each of the components of the expression construct is amplified from a suitable template nucleic acid using, for example, PCR and subsequently cloned into a suitable expression construct, such as for example, a plasmid or a phagemid.

Vectors suitable for such an expression construct are known in the art and/or described herein. For example, an expression vector suitable for the method of the present disclosure in a mammalian cell is, for example, a vector of the pcDNA vector suite supplied by Invitrogen, a vector of the pCI vector suite (Promega), a vector of the pCMV vector suite (Clontech), a pM vector (Clontech), a pSI vector (Promega), a VP 16 vector (Clontech) or a vector of the pcDNA vector suite (Invitrogen).

The skilled artisan will be aware of additional vectors and sources of such vectors, such as, for example, Life Technologies Corporation, Clontech or Promega.

Means for introducing the isolated nucleic acid molecule or a gene construct comprising same into a cell for expression are known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD. USA), PEG-mediated DNA uptake, electroporation and microparticle bombardment such as by using DNA-coated tungsten or gold particles (Agracetus Inc., WI, USA) amongst others.

Alternatively, an expression construct of the disclosure is a viral vector. Suitable viral vectors are known in the art and commercially available. Conventional viral-based systems for the delivery of a nucleic acid and integration of that nucleic acid into a host cell genome include, for example, a retroviral vector, a lentiviral vector or an adeno-associated viral vector. Alternatively, an adenoviral vector is useful for introducing a nucleic acid that remains episomal into a host cell. Viral vectors are an efficient and versatile method of gene transfer in target cells and tissues. Additionally, high transduction efficiencies have been observed in many different cell types and target tissues.

For example, a retroviral vector generally comprises cis-acting long terminal repeats (LTRs) with packaging capacity for up to 6-10 kb of foreign sequence. The minimum cis-acting LTRs are sufficient for replication and packaging of a vector, which is then used to integrate the expression construct into the target cell to provide long term expression. Widely used retroviral vectors include those based upon murine leukemia virus (MuLV), gibbon ape leukemia virus (GaLV), simian immunodeficiency virus (SrV), human immunodeficiency virus (HIV), and combinations thereof (see, e.g., Buchscher et al., *J Virol.* 56:2731-2739 (1992); Johann et al, *J. Virol.* 65:1635-1640 (1992); Sommerfelt et al, *Virol.* 76:58-59 (1990); Wilson et al, *J. Virol.* 63:274-2318 (1989); Miller et al., *J. Virol.* 65:2220-2224 (1991); PCT/US94/05700; Miller and Rosman *Bio-*

Techniques 7:980-990, 1989; Miller, A. D. *Human Gene Therapy* 7:5-14, 1990; Scarpa et al *Virology* 75:849-852, 1991; Burns et al. *Proc. Natl. Acad. Sci USA* 90:8033-8037, 1993).

Various adeno-associated virus (AAV) vector systems have also been developed for nucleic acid delivery. AAV vectors can be readily constructed using techniques known in the art. See, e.g., U.S. Pat. Nos. 5,173,414 and 5,139,941; International Publication Nos. WO 92/01070 and WO 93/03769; Lebkowski et al. *Molec. Cell. Biol.* 5:3988-3996, 1988; Vincent et al. (1990) Vaccines 90 (Cold Spring Harbor Laboratory Press); Carter *Current Opinion in Biotechnology* 5:533-539, 1992; Muzyezka. *Current Topics in Microbiol, and Immunol.* 158:97-129, 1992; Kotin, Human Gene Therapy 5:793-801, 1994; Shelling and Smith *Gene Therapy* 7:165-169, 1994; and Zhou et al. *J. Exp. Med.* 179:1867-1875, 1994.

Additional viral vectors useful for delivering an expression construct of the disclosure include, for example, those derived from the pox family of viruses, such as vaccinia virus and avian poxvirus or an alphavirus or a conjugate virus vector (e.g. that described in Fisher-Hoch et al., *Proc. Natl Acad. Sci. USA* 56:317-321, 1989).

Assaying Therapeutic/Prophylactic Potential of Cells and Soluble Factors

Methods for determining the ability of cells or soluble factors to treat or prevent or delay the onset or progression of disorders associated with low osteoblast levels or activity will be apparent to the skilled artisan.

For example, cells or soluble factors are assessed for their ability to increase osteoblastic function.

In one example, osteoprogenitor cells (e.g., expressing Cbfe1/RunX2) are contacted with the cells and/or soluble factors and tested for their ability to differentiate into osteoblasts. For example, the cells are assessed for development of expression of osterix and/or ColI and/or BSP and/or M-CSF and/or alkaline phosphatase.

In one example, the cells and/or soluble factors are contacted to osteoblasts and their effect on production of type I collagen and/or osteocalcin is assessed, e.g., using an immunoassay and/or immunohistochemistry or immunofluorescence.

In a further example, the cells and/or soluble factors are contacted to osteoblasts cultured on an extracellular matrix and their ability to increase mineralization of the matrix is assessed, e.g., by staining with Alziarin Red or von Kossa stain.

The cells and/or soluble factors can also be assessed for their effect on osteoblast activity in vivo using an assay such as near-infrared fluorescence imaging, e.g., as described in Zaheer et al., *Nat. Biotechnol.*, 19: 1148-1154, 2001.

The cells and/or soluble factors can also be assessed for their effect on osteoblast activity in vivo by detecting their effect on bone formation, e.g., using x-ray and/or dual energy X-ray absorptiometry (DEXA).

For example, cells or soluble factors (e.g., a mixture of factors or a single factor or a fraction of factors (e.g., derived by affinity purification or chromatography) are administered to a model of a metabolic bone disorder and the effect on one or more symptoms is assessed. Exemplary non-human animal models include ovariectomized rodents (e.g., rats), immobilization-induced bone loss models and/or models reviewed in Turner *European Cells and Materials*, 1: 66-91, 2001.

It will be apparent to the skilled artisan from the foregoing that the present disclosure also provides a method for identifying or isolating a cell or a soluble factor for the treatment, prevention or delay of a disorder associated with low osteoblast levels or activity, the method comprising:

(i) administering a cell or a soluble factor to a test subject suffering from disorder associated with low osteoblast levels or activity and assessing a symptom of the disorder in the subject;

(ii) comparing the symptom of a disorder associated with low osteoblast levels or activity of the subject at (i) to the symptom of the disorder associated with low osteoblast levels or activity of a control subject suffering from the disorder to which the cell or soluble factor has not been administered.

wherein an improvement in the symptom in the test subject compared to the control subject indicates that the cell or soluble factor treats the disorder.

The cell may be any cell described herein according to any example.

Cellular Compositions

In one example of the present disclosure stem cells and/or progeny cells thereof are administered in the form of a composition. In one example, such a composition comprises a pharmaceutically acceptable carrier and/or excipient.

The terms "carrier" and "excipient" refer to compositions of matter that are conventionally used in the art to facilitate the storage, administration, and/or the biological activity of an active compound (see, e.g., Remington's Pharmaceutical Sciences, 16th Ed., Mac Publishing Company (1980). A carrier may also reduce any undesirable side effects of the active compound. A suitable carrier is, for example, stable, e.g., incapable of reacting with other ingredients in the carrier. In one example, the carrier does not produce significant local or systemic adverse effect in recipients at the dosages and concentrations employed for treatment.

Suitable carriers for the present disclosure include those conventionally used, e.g., water, saline, aqueous dextrose, lactose, Ringer's solution, a buffered solution, hyaluronan and glycols are exemplary liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

In another example, a carrier is a media composition, e.g., in which a cell is grown or suspended. For example, such a media composition does not induce any adverse effects in a subject to whom it is administered.

Exemplary carriers and excipients do not adversely affect the viability of a cell and/or the ability of a cell to reduce, prevent or delay metabolic syndrome and/or obesity.

In one example, the carrier or excipient provides a buffering activity to maintain the cells and/or soluble factors at a suitable pH to thereby exert a biological activity, e.g., the carrier or excipient is phosphate buffered saline (PBS). PBS represents an attractive carrier or excipient because it interacts with cells and factors minimally and permits rapid release of the cells and factors, in such a case, the composition of the disclosure may be produced as a liquid for direct application to the blood stream or into a tissue or a region surrounding or adjacent to a tissue, e.g., by injection.

Stem cells and/or progeny cells thereof can also be incorporated or embedded within scaffolds that are recipient-compatible and which degrade into products that are not harmful to the recipient. These scaffolds provide support and protection for cells that are to be transplanted into the recipient subjects. Natural and/or synthetic biodegradable scaffolds are examples of such scaffolds.

A variety of different scaffolds may be used successfully in the practice of the disclosure. Exemplary scaffolds include, but are not limited to biological, degradable scaffolds. Natural biodegradable scaffolds include collagen, fibronectin, and laminin scaffolds. Suitable synthetic material for a cell transplantation scaffold should be able to support extensive cell growth and cell function. Such scaffolds may also be resorbable. Suitable scaffolds include polyglycolic acid scaffolds, e.g., as described by Vacanti, et al. *J. Ped. Surg.* 23:3-9 1988; Cima, et al. *Biotechnol. Bioeng.* 38:145 1991; Vacanti, et al. *Plast. Reconsnr. Surg.* 88:753-9 1991; or synthetic polymers such as polyanhydrides, polyorthoesters, and polylactic acid.

In another example, the cells may be administered in a gel scaffold (such as Gelfoam from Upjohn Company.

The cellular compositions useful for methods described herein may be administered alone or as admixtures with other cells. Cells that may be administered in conjunction with the compositions of the present disclosure include, but are not limited to, other multipotent or pluripotent cells or stem cells, or bone marrow cells. The cells of different types may be admixed with a composition of the disclosure immediately or shortly prior to administration, or they may be co-cultured together for a period of time prior to administration.

In one example, the composition comprises an effective amount or a therapeutically or prophylactically effective amount of cells. For example, the composition comprises about $1\times10^5$ stem cell (such as STRO-$1^+$ cells)/kg to about $1\times10^7$ stem cell (such as STRO-$1^+$ cells)/kg or about $1\times10^6$ stem cell (such as STRO-1+ cells)/kg to about $5\times10^6$ stem cell (such as STRO-$1^+$ cells)/kg. The exact amount of cells to be administered is dependent upon a variety of factors, including the age, weight, and sex of the patient, and the extent and severity of the disorder associated with low osteoblast levels or activity.

In one example, a low dose of cells is administered to the subject. Exemplary dosages include between about $0.1\times10^4$ and $0.5\times10^6$ cells per kg, for example, between about $0.1\times10^5$ and $0.5\times10^6$ cells per kg, such as, between about $0.5\times10^5$ and $0.5\times10^6$ cells per kg, for example, between about $0.1\times10^6$ and $0.5\times10^6$ cells per kg, e.g., about $0.2\times10^6$ or $0.3\times10^6$ or $0.4\times10^6$ cells per kg.

In some examples, cells are contained within a chamber that does not permit the cells to exit into a subject's circulation, however that permits factors secreted by the cells to enter the circulation. In this manner soluble factors may be administered to a subject by permitting the cells to secrete the factors into the subject's circulation. Such a chamber may equally be implanted at a site in a subject to increase local levels of the soluble factors, e.g., implanted in or near a pancreas.

In some examples of the disclosure, it may not be necessary or desirable to immunosuppress a patient prior to initiation of therapy with cellular compositions. Accordingly, transplantation with allogenic, or even xenogeneic, stem cells or progeny thereof may be tolerated in some instances.

However, in other instances it may be desirable or appropriate to pharmacologically immunosuppress a patient prior to initiating cell therapy and/or reduce an immune response of a subject against the cellular composition. This may be accomplished through the use of systemic or local immunosuppressive agents, or it may be accomplished by delivering the cells in an encapsulated device. The cells may be encapsulated in a capsule that is permeable to nutrients and oxygen required by the cell and therapeutic factors the cell is yet impermeable to immune humoral factors and cells. In one example, the encapsulant is hypoallergenic, is easily and stably situated in a target tissue, and provides added protection to the implanted structure. These and other means for reducing or eliminating an immune response to the transplanted cells are known in the art. As an alternative, the cells may be genetically modified to reduce their immunogenicity.

Compositions of Soluble Factors

In one example of the present disclosure, stem cell-derived and/or progeny cell-derived supernatant or soluble factors are administered in the form of a composition, e.g., comprising a suitable carrier and/or excipient. In one example, the carrier or excipient does not adversely affect the biological effect of the soluble factors or supernatant.

In one example, the composition comprises a composition of matter to stabilize a soluble factor or a component of supernatant, e.g., a protease inhibitor. In one example, the protease inhibitor is not included in an amount sufficient to have an adverse effect on a subject.

Compositions comprising stem cell-derived and/or progeny cell-derived supernatant or soluble factors may be prepared as appropriate liquid suspensions, e.g., in culture medium or in a stable carrier or a buffer solution, e.g., phosphate buffered saline. Suitable carriers are described herein above. In another example, suspensions comprising stem cell-derived and/or progeny cell-derived supernatant or soluble factors are oily suspensions for injection. Suitable lipophilic solvents or vehicles include fatty oils such as sesame oil; or synthetic fatty acid esters, such as ethyl oleate or triglycerides; or liposomes. Suspensions to be used for injection may also contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Sterile injectable solutions can be prepared by incorporating the supernatant or soluble factors in the required amount in an appropriate solvent with one or a combination of ingredients described above, as required, followed by filtered sterilization.

Generally, dispersions are prepared by incorporating the supernatant or soluble factors into a sterile vehicle that contains a basic dispersion medium and the required other ingredients from those enumerated above. In the case of sterile powders for the preparation of sterile injectable solutions, exemplary methods of preparation are vacuum drying and freeze-drying which yields a powder of the active ingredient plus any additional desired ingredient from a previously sterile-filtered solution thereof. In accordance with an alternative aspect of the disclosure, the supernatant or soluble factors may be formulated with one or more additional compounds that enhance its solubility.

Other exemplary carriers or excipients are described, for example, in Hardman, et al. (2001) Goodman and Gilman's The Pharmacological Basis of Therapeutics, McGraw-Hill, New York, N. Y.; Gennaro (2000) Remington: The Science and Practice of Pharmacy, Lippincott, Williams, and Wilkins, New York, N. Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N. Y.

Therapeutic compositions typically should be sterile and stable under the conditions of manufacture and storage. The composition can be formulated as a solution, microemulsion, liposome, or other ordered structure. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In some cases, isotonic agents are included, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the soluble factors may be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

The supernatant or soluble factors may be administered in combination with an appropriate matrix, for instance, to provide slow release of the soluble factors.

Additional Components of Compositions

The stem cell-derived supernatant or soluble factors, stem cells or progeny thereof may be administered with other beneficial drugs or biological molecules (growth factors, trophic factors). When administered with other agents, they may be administered together in a single pharmaceutical composition, or in separate pharmaceutical compositions, simultaneously or sequentially with the other agents (either before or after administration of the other agents). Bioactive factors which may be co-administered include anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST, TRANILAST, REMICADE, SIROLIMUS, and NSAIDs (non-steroidal anti-inflammatory drugs; e.g., TEPOXALIN, TOLMETIN, SUPROFEN); immunosuppressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine) as well as local anesthetics.

In one example, a composition as described herein according to any example comprises an additional factor for the treatment or prophylaxis of a disorder associated with low osteoblast levels or activity.

Alternatively, or in addition, cells, secreted factors and/or a composition as described herein according to any example is combined with a known treatment of a disorder associated with low osteoblast levels or activity.

In one example, a pharmaceutical composition as described herein according to any example comprises a compound used to a disorder associated with low osteoblast levels or activity. Alternatively, a method of treatment/prophylaxis as described herein according to any embodiment additionally comprises administering a compound used to treat a disorder associated with low osteoblast levels or activity. Exemplary compounds are described herein and are to be taken to apply mutatis mutandis to these examples of the present disclosure.

In another example, a composition as described herein according to any example additionally comprises a factor that induces or enhances differentiation of a progenitor cell into a vascular cell. Exemplary factors include, vascular endothelial growth factor (VEGF), platelet derived growth factor (PDGF; e.g., PDGF-BB), and FGF.

In another example, a composition as described herein according to any example additionally comprises a tissue specific committed cell (TSCC). In this respect, International Patent Application No. PCT/AU2005/001445 demonstrates that administration of a TSCC and a STRO-1$^+$ cells can lead to enhanced proliferation of the TSCC. In one example, the TSCC is a vascular cell. Administration of such a composition to a subject may lead to increased production of vasculature, e.g., leading to increased nutrients being delivered to the affected tissue.

Medical Devices

The present disclosure also provides medical devices for use or when used in a method as described herein according to any example. For example, the present disclosure provides a syringe or catheter or other suitable delivery device comprising stem cells and/or progeny cells thereof and/or soluble factors therefrom and/or a composition as described herein according to any example. Optionally, the syringe or catheter is packaged with instructions for use in a method as described herein according to any example.

In another example, the present disclosure provides an implant comprising stem cells and/or progeny cells thereof and/or soluble factors therefrom and/or a composition as described herein according to any example. Optionally, the implant is packaged with instructions for use in a method as described herein according to any example. Suitable implants may be formed with a scaffold, e.g., as described herein above and stem cells and/or progeny cells thereof and/or soluble factors therefrom.

Modes of Administration

In on example, the stem cell-derived supernatant or soluble factors, stem cells or progeny thereof is/are delivered to the blood stream of a subject. For example, the stem cell-derived supernatant or soluble factors, stem cells or progeny thereof are delivered parenterally. Exemplary routes of parenteral administration include, but are not limited to, intraperitoneal, intraventricular, intracerebroventricular, intrathecal, or intravenous. In one example, the stem cell-derived supernatant or soluble factors, stem cells or progeny thereof are delivered intra-arterially, into an aorta, into an atrium or ventricle of the heart or into a blood vessel, e.g., intravenously.

In the case of cell delivery to an atrium or ventricle of the heart, cells can be administered to the left atrium or ventricle to avoid complications that may arise from rapid delivery of cells to the lungs.

In one example, the stem cell-derived supernatant or soluble factors, stem cells or progeny thereof are delivered intravenously.

In one example, the stem cell-derived supernatant or soluble factors, stem cells or progeny thereof are injected into the site of delivery, e.g., using a syringe or through a catheter or a central line.

Selecting an administration regimen for a therapeutic formulation depends on several factors, including the serum or tissue turnover rate of the entity, the level of symptoms, and the immunogenicity of the entity. In one example, an administration regimen maximizes the amount of therapeutic compound delivered to the patient consistent with an acceptable level of side effects. Accordingly, the amount of formulation delivered depends in part on the particular entity and the severity of the condition being treated.

In one example, stem cell-derived supernatant or soluble factors, stem cells or progeny thereof are delivered as a single bolus dose. Alternatively, stem cell-derived supernatant or soluble factors, stem cells or progeny thereof are administered by continuous infusion, or by doses at intervals of, e.g., one day, one week, or 1-7 times per week. An exemplary dose protocol is one involving the maximal dose or dose frequency that avoids significant undesirable side effects. A total weekly dose depends on the type and activity of the compound/cell being used. Determination of the appropriate dose is made by a clinician, e.g., using parameters or factors known or suspected in the art to affect treatment or predicted to affect treatment. Generally, the dose begins with an amount somewhat less than the optimum dose and is increased by small increments thereafter until the desired or optimum effect is achieved relative to any negative side effects.

The present inventors have shown therapeutic benefits provided by stem cells and/or progeny thereof and/or soluble factors derived therefrom are observed for at least four weeks in a subject. Accordingly, in some examples the cells are administered weekly, fortnightly, once every three weeks or once every four weeks.

In accordance with examples of the disclosure directed to treating or delaying the progression of a disorder associated with low osteoblast levels or activity, stem cells and/or progeny cells thereof and/or soluble factors derived therefrom are administered following diagnosis of the disorder, e.g., using standard methods known in the art and/or described herein.

For those examples directed to preventing or delaying the onset of a disorder associated with low osteoblast levels or activity, the stem cells and/or progeny cells thereof and/or soluble factors derived therefrom can administered prior to clinical diagnosis of the disorder.

The present disclosure includes the following non-limiting examples.

EXAMPLES

Example 1: Immunoselection of MPCs by Selection of STRO-3 Cells

Bone marrow (BM) is harvested from healthy normal adult volunteers (20-35 years old). Briefly, 40 ml of BM is aspirated from the posterior iliac crest into lithium-heparin anticoagulant-containing tubes.

BMMNC are prepared by density gradient separation using Lymphoprep™ (Nycomed Pharma, Oslo, Norway) as previously described (Zannettino, A. C. et al. (1998) *Blood* 92: 2613-2628). Following centrifugation at 400×g for 30 minutes at 4° C., the buffy layer is removed with a transfer pipette and washed three times in "HHF", composed of Hank's balanced salt solution (HBSS; Life Technologies, Gaithersburg, Md.), containing 5% fetal calf serum (FCS, CSL Limited, Victoria, Australia).

STRO-3$^+$ (or TNAP$^+$) cells were subsequently isolated by magnetic activated cell sorting as previously described (Gronthos et al. (2003) *Journal of Cell Science* 116: 1827-1835; Gronthos, S. and Simmons, P. J. (1995) *Blood* 85: 929-940). Briefly, approximately 1-3×10$^8$ BMMNC are incubated in blocking buffer, consisting of 10% (v/v) normal rabbit serum in HHF for 20 minutes on ice. The cells are incubated with 200 μl of a 10 μg/ml solution of STRO-3 mAb in blocking buffer for 1 hour on ice. The cells are subsequently washed twice in HHF by centrifugation at 400×g. A 1/50 dilution of goat anti-mouse γ-biotin (Southern Biotechnology Associates, Birmingham, UK) in HHF buffer is added and the cells incubated for 1 hour on ice. Cells are washed twice in MACS buffer (Ca$^{2+}$ and Mn$^{2+}$-free PBS supplemented with 1% BSA, 5 mM EDTA and 0.01% sodium azide) as above and resuspended in a final volume of 0.9 ml MACS buffer.

One hundred μl streptavidin microbeads (Miltenyi Biotec; Bergisch Gladbach, Germany) are added to the cell suspension and incubated on ice for 15 minutes. The cell suspension is washed twice and resuspended in 0.5 ml of MACS buffer and subsequently loaded onto a mini MACS column (MS Columns, Miltenyi Biotec), and washed three times with 0.5 ml MACS buffer to retrieve the cells which did not bind the STRO-3 mAb (deposited on 19 Dec. 2005 with American Type Culture Collection (ATCC) under accession number PTA-7282—see International Publication No. WO 2006/108229). After addition of a further 1 ml MACS buffer, the column is removed from the magnet and the TNAP$^+$ cells are isolated by positive pressure. An aliquot of cells from each fraction can be stained with streptavidin-FITC and the purity assessed by flow cytometry.

Example 2: Cells Selected by STRO-3 mAb are STRO-1$^{bright}$ Cells

Experiments were designed to confirm the potential of using STRO-3 mAb as a single reagent for isolating cells STRO-1$^{bright}$ cells.

Given that STRO-3 (IgG1) is a different isotype to that of STRO-1 (IgM), the ability of STRO-3 to identify clonogenic CFU-F was assessed by two-color FACS analysis based on its co-expression with STRO-1$^+$ cells isolated using the MACS procedure (FIG. 1). The dot plot histogram represents 5×10$^4$ events collected as listmode data. The vertical and horizontal lines were set to the reactivity levels of <1.0% mean fluorescence obtained with the isotype-matched control antibodies, 1B5 (IgG) and 1A6.12 (IgM) treated under the same conditions. The results demonstrate that a minor population of STRO-1$^{bright}$ cells co-expressed TNAP (upper right quadrant) while the remaining STRO-1$^+$ cells failed to react with the STRO-3 mAb. Cells isolated by FACS from all four quadrants were subsequently assayed for the incidence of CFU-F (Table 1).

TABLE 1

Enrichment of human bone marrow cells by dual-color FACS analysis based on the co-expression of the cell surface markers STRO-1 and TNAP (refer to FIG. 1). FACS sorted cells were cultured under standard clonogenic conditions in alpha MEM supplemented with 20% FCS. The data represents the mean number of day 14 colony-forming cells (CFU-F) per $10^5$ cells plated ± SE (n = 3 different bone marrow aspirates). These data suggest that human MPC are exclusively restricted to the TNAP positive fraction of BM which co-express the STRO-1 antigen brightly.

| Bone Marrow Fraction | Frequency of CFU-F/$10^5$ Cells | Enrichment (Fold Increase) |
|---|---|---|
| Unfractionated BMMNC | 11.0 ± 2.2 | 1.0 |
| TNAP$^+$/STRO-1$^{bright}$ | 4,511 ± 185 | 410 |
| TNAP$^+$/STRO-1$^{dull}$ | 0.0 | 0.0 |

Example 3: Characterization of Cynomolgus Monkey STRO-3$^+$ MPCs

Simian marrow progenitor cells (from cynomolgus monkeys; cyno-MPC) were isolated from ~15 ml of bone marrow aspirate collected from a female *Macaca fascicularis*. The marrow aspirate suspension was separated using a Ficoll gradient and washed to remove non-nucleated cells (red blood cells). The nucleated cells were counted and separated by attaching CA12 antibody (anti-STRO-3) and Dynalbeads. The cells with antibody and beads attached were positively selected by the magnetic field of an MPC-1 magnet. The positive selected cells were counted and seeded into T-flasks at passage (p.) 0 in Growth Medium. Preselection, positive, and negative cells were used in a colony forming assay (CFU-F).

The cyno-MPC cells were fed with Growth Media. All cultures (p.0-p.5) were fed every 2 to 4 days until they reached desired confluence. The cells were then passaged or harvested using HBSS wash and then collagenase followed by Trypsin/Versene. The p.1 cells were counted and seeded into T-flasks. When the p.1 cyno-MPC reached desired confluence the cells were harvested and cryopreserved using a controlled rate freezer.

Passage 1 cryopreserved cyno-MPC were thawed and seeded into T-flasks (p.2). The p.2 cells were passaged into a Cell Factory at p.3. The p.3 cells were harvested and passaged to p.4 in to a Cell Factory. Extra p.3 cells were cryopreserved. The p.4 cells were passaged to 6× Cell Factories at p.5. When the p.5 cyno-MPC reached desired confluence the cells were harvested and cryopreserved using a controlled rate freezer. The cells were cryopreserved in 50% AlphaMEM, 42.5% Profreeze, and 7.5% DMSO. Samples were tested for CFU-F assay, FACS, sterility, mycoplasma, and endotoxin.

Figure 2:
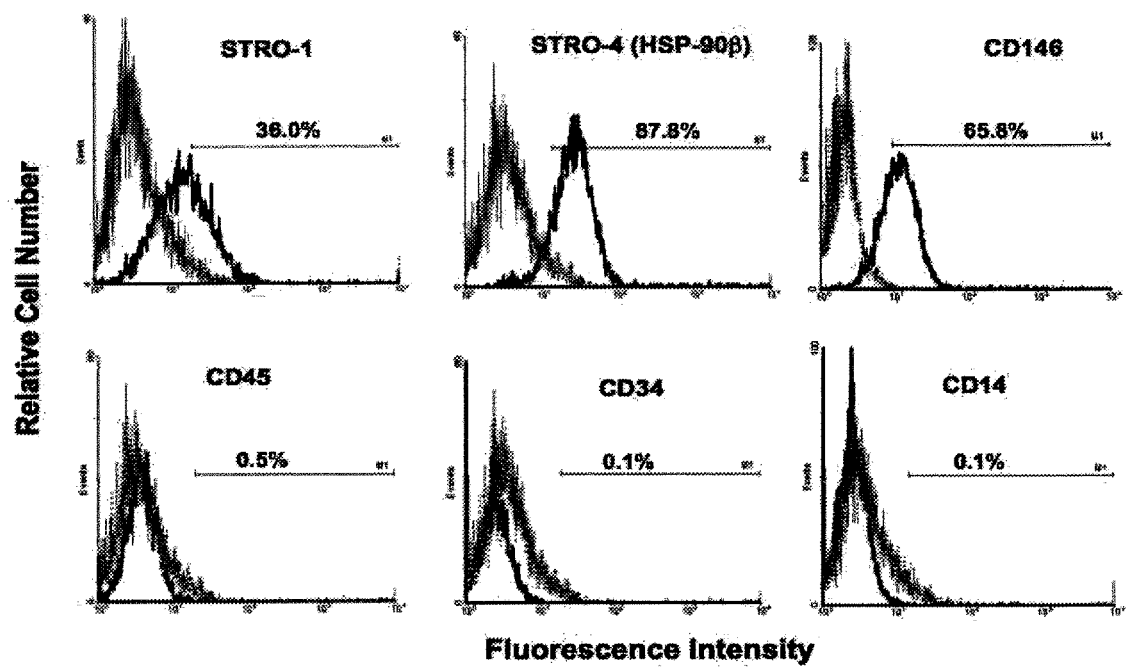
FIG. 2. Graphical representations showing representative flow cytometric histograms produced using single cell suspensions of culture expanded bone marrow derived cynomolgus MPCs with positive cell surface expression of the mesenchymal stem cell markers, STRO-1, STRO-4 and CD146 (solid) relative to the isotype (IgM, IgG2a and IgG1) negative controls (hashed) detected using goat anti-murine IgM or IgG conjugated-FITC secondary antibodies. Representative histograms also show that cynomolgus MPCs lack cell surface expression for markers of monocyte/macrophage (CD14), haematopoietic stem/progenitor cells (CD34) and mature leukocyte (CD45). Levels of greater than 1% fluorescence compared to the isotype control signify positivity.

Results of representative flow cytometry analysis of the immunophenotype of cultured cyno-MPCs are shown in FIG. 2. As shown, these cells are STRO-1$^+$, STRO-4$^+$ and CD146$^+$.

Cyno MPC at p5 were thawed and used for the intravenous injection of diabetic and non-diabetic cynomolgous monkeys as described in Example 4.

Example 4: Effect of Systemic Administration of MPCs on Blood Osteocalcin Levels in Obese Monkeys Five (5) cynomolgous monkeys were selected for treatment based on the following criteria: (i) age >14 years, (ii) high fasting blood glucose (>105 mg/dL), fasting blood insulin level (<60 mU/L) (iii) high BMI (>46 males >24 females)), (iv) greater than 8 kg body weight males and >3.5 kg body weight for females, (v) high fasting triglyceride; and (vi) blunted phase I insulin response based on IVGTT.

The monkeys were assigned to Groups 1, 2 or 3. Animals received a single slow intravenous (IV) infusion of allogeneic MPC (isolated as described in Example 2) into the cephalic vein or a suitable peripheral vein at a dose as follows (dose was adjusted to the latest body weight recorded):

TABLE 3

Summary of treatment groups

| Group | Dose level | Dose MPC/kg | Route |
|---|---|---|---|
| 1 (#2875, #1880) | Low | 0.3 × $10^6$ | IV |
| 2 (#1624, #3351) | Mid | 1 × $10^6$ | IV |
| 3 (#7581) | High | 2 × $10^6$ | IV |

Figure 3:
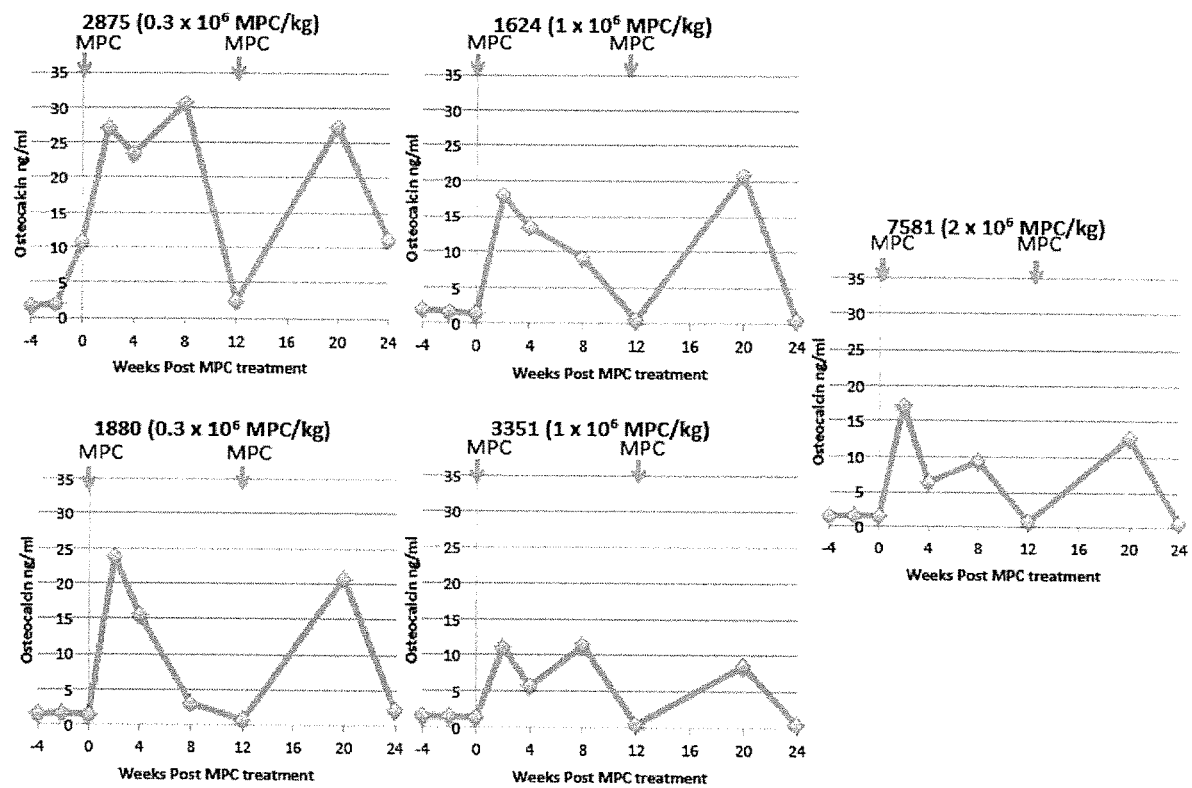
FIG. 3. Graphical representation of the fasting profile for blood osteocalcin (ng/ml) monitored over a period of 6 months following IV injection of allogeneic MPC for individual animals. Arrows indicate the time of administration of a single dose of MPC.
Figure 10:
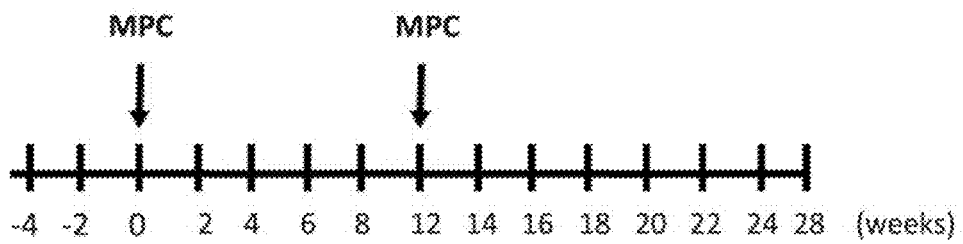
FIG. 10. Graphical representation showing time of first and second MPC infusions administered intravenously to Obese Mauritian Cynomolgous Monkeys.

Each monkey received a first infusion of MPC at week 0 and a second infusion at week 12 as shown in FIG. 10. Osteocalcin sampling occurred at weeks: −4, −2, 0, 2, 4, 8, 12, 20, 24
Alkaline Phosphatase sampling occurred at weeks: −2, 2, 4, 6, 8, 12, 14, 16, 18, 20, 22, 24.
Results The fasting profile for blood osteocalcin (ng/ml) was monitored over a period of 6 months following IV injection of allogeneic MPC for individual animals. Results are shown in FIG. 3 where arrows indicate the time of administration of a single dose of MPC.

All 5 animals showed low plasma levels of osteocalcin prior to MPC treatment with a mean baseline value of 1.4 (+/−1.5, SEM) ng/ml.

Figure 4:
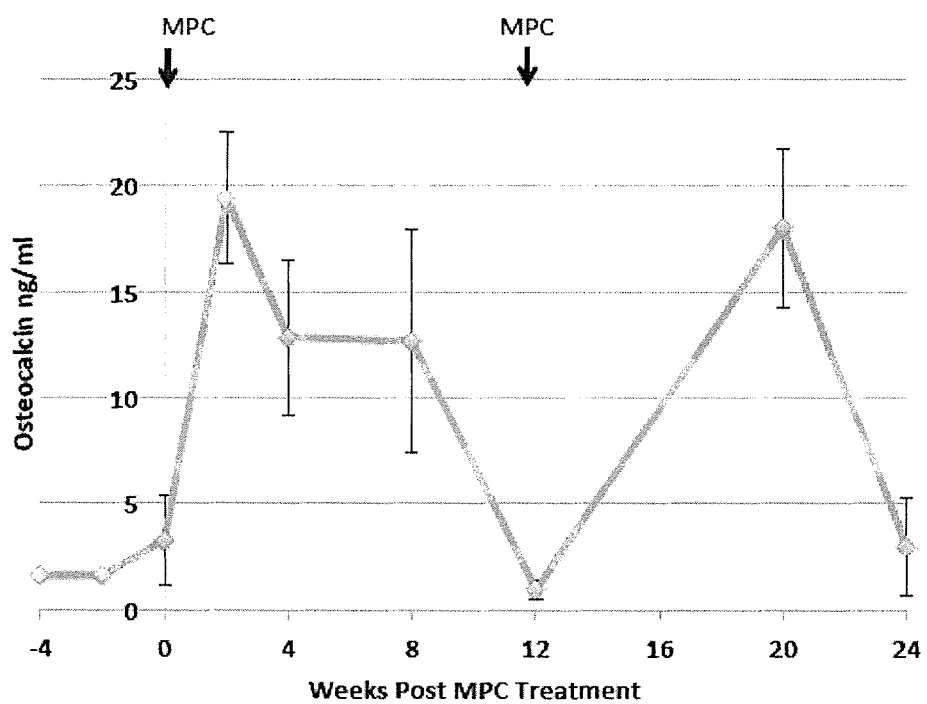
FIG. 4. Graphical representation of mean profiles for plasma osteocalcin levels following two single doses of MPC administered intravenously to Obese Mauritian Cynomolgous Monkeys.

The data show that the osteocalcin response occurs within 2 weeks after each injection, and the effect has a duration of 12 weeks. The data also show that repeat injections of MPCs are at least as effective as initial injections. Peak osteocalcin values ranged from 10 to 30 ng/ml. Maximal osteocalcin induction was seen at the lowest cell doses tested FIG. 4 shows that the osteocalcin response is observed within 2 weeks after the 1st MPC injection in obese Mauritian cynomolgous monkeys. Following a peak response at 2-8 weeks values return to baseline by 12 weeks. Interestingly, the second MPC injection demonstrates a similar kinetics as the first injection maintaining the same level osteocalcin response.

Figure 5:
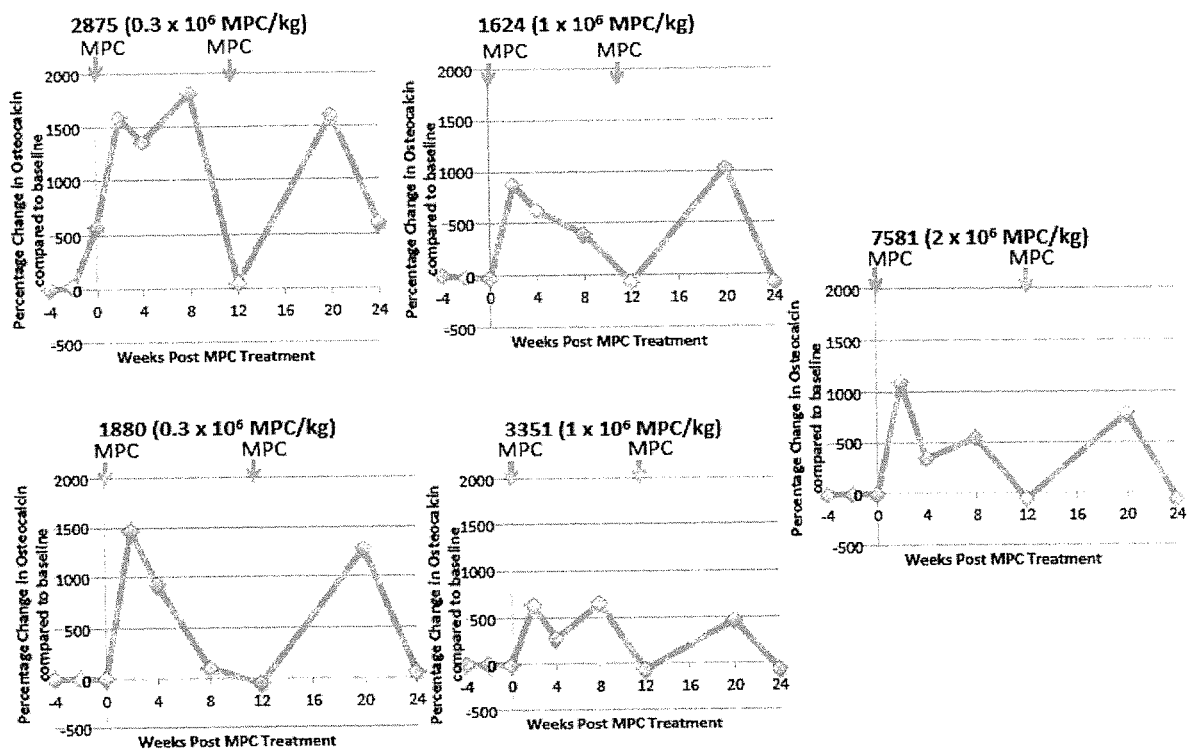
FIG. 5. Graphical representation showing percentage changes in osteocalcin levels following MPC treatment compared to baseline levels prior to treatment.

FIG. 5 demonstrates the percentage change in osteocalcin response over a 6 month period relative to the baseline at week 0. The most profound responses were noted with the low dose of MPC injection (0.3 million MPC/kg).

Figure 6:
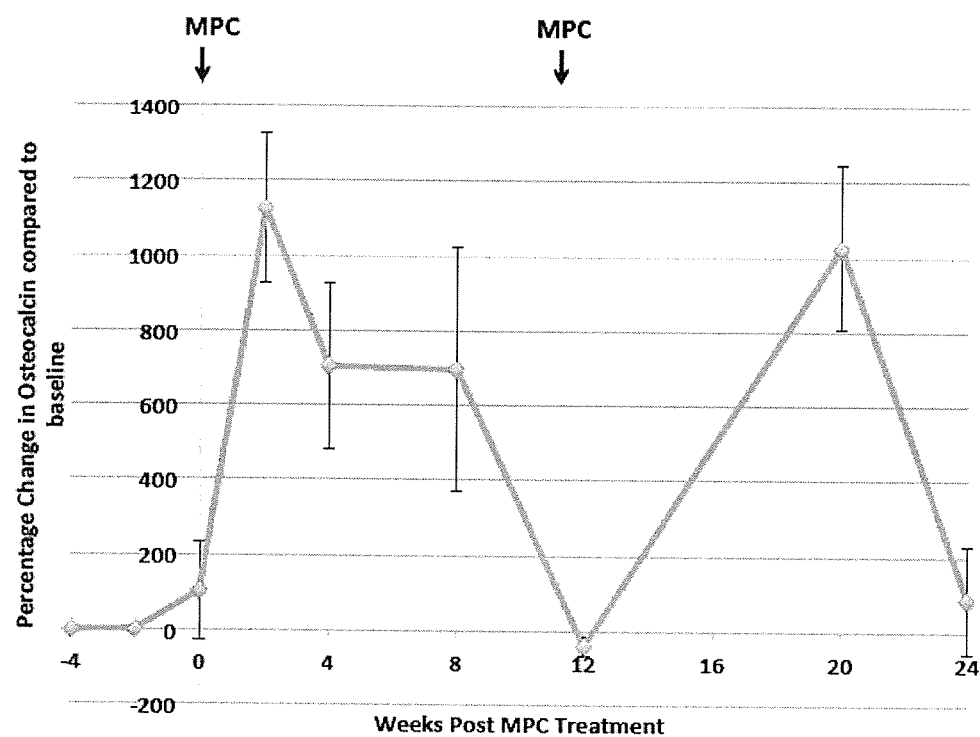
FIG. 6. Graphical representation showing mean percentage changes .m osteocalcin levels following MPC treatment compared to baseline levels prior to treatment.

FIG. 6 shows the mean percentage changes in osteocalcin levels following MPC treatment compared to baseline levels prior to treatment. The mean percentage increase in osteocalcin from baseline peaked at week 2 with a value of 1134% (+/−202). The amplitude of the responses after the second injection appear to be similar to that of the first MPC injection.

Figure 7:
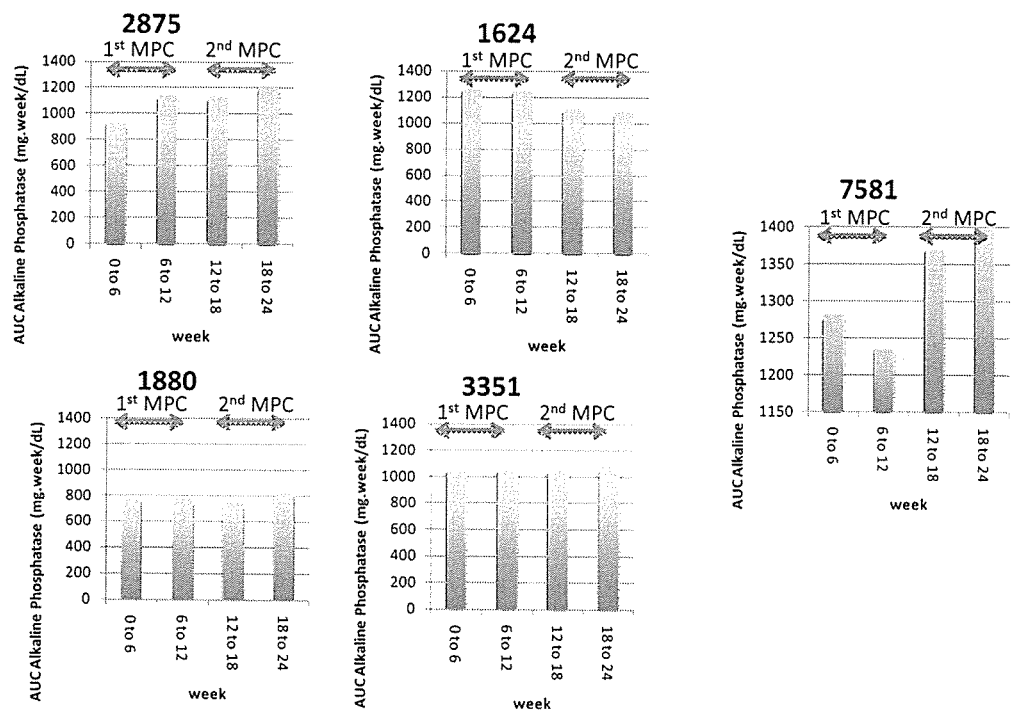
FIG. 7. Graphical representation showing 4/5 animals demonstrate progressive increase in plasma total alkaline phosphatase over 6 months of MPC treatment (as measured by Area Under the Curve analysis).

FIG. 7 shows a progressive increase in plasma alkaline phosphatase over 6 months of MPC treatment (as measured by Area Under the Curve analysis).

Figure 8:
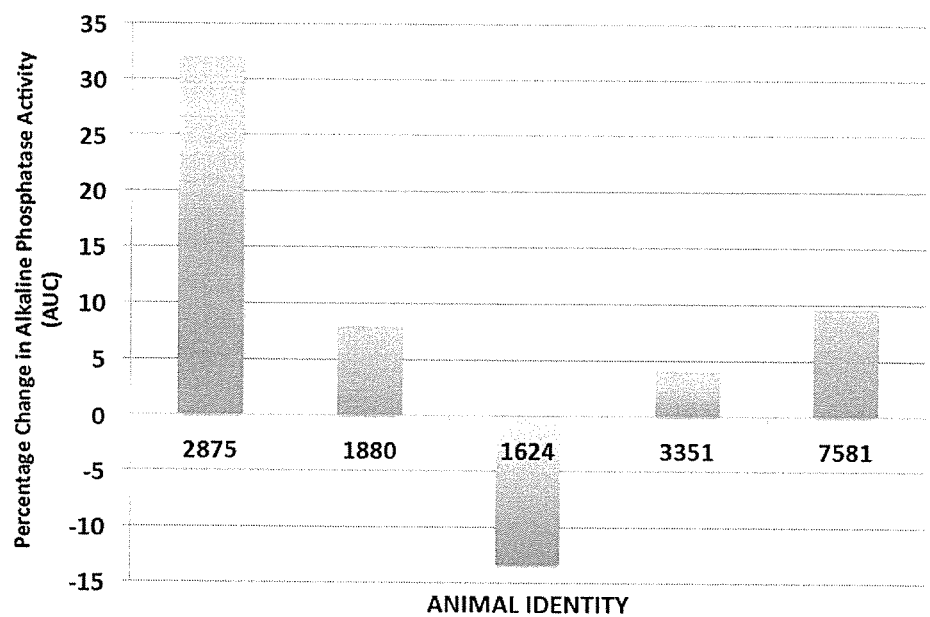
FIG. 8. Graphical representation showing 4/5 animals demonstrate progressive increase in plasma total alkaline phosphatase over 6 months of MPC treatment (as measured by % increase in Area Under the Curve analysis between 18-24 weeks versus 0-6 weeks).
Figure 9:
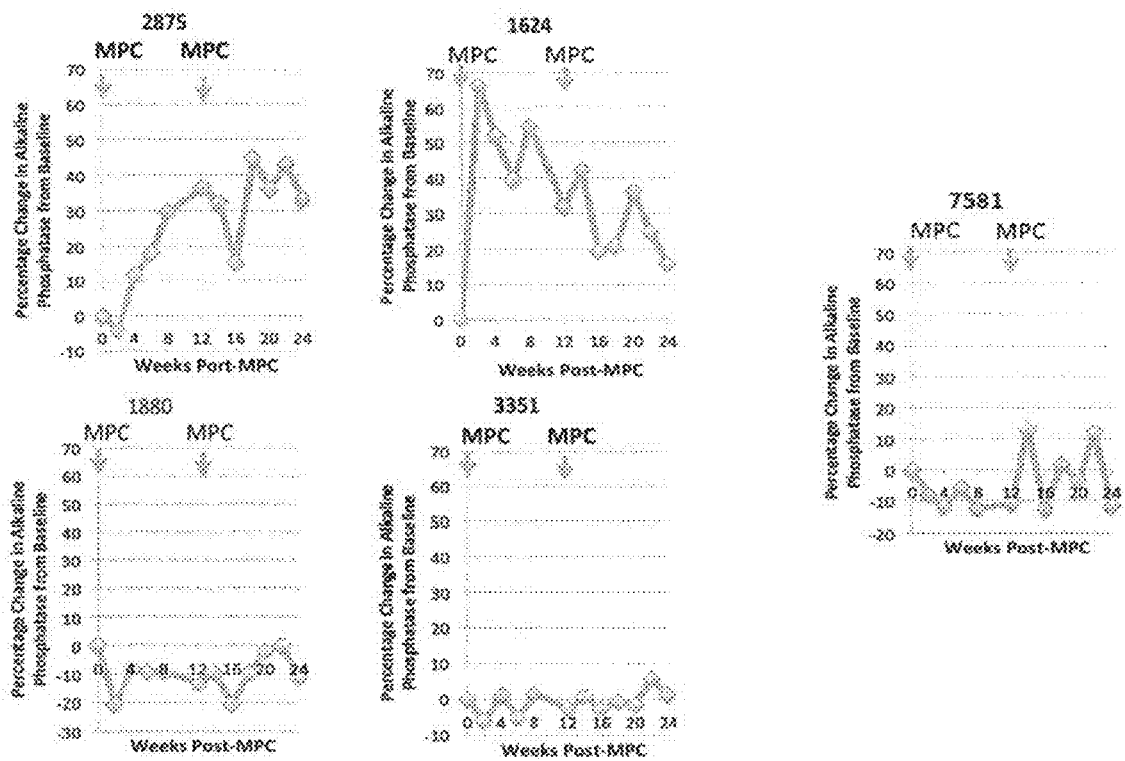
FIG. 9. Graphical representation showing percentage changes in alkaline phosphatase levels following MPC treatment compared to baseline levels prior to treatment in individual animals.

FIG. 8 shows a progressive increase in plasma total alkaline phosphatase over 6 months of MPC treatment (as measured by % increase in Area Under the Curve analysis between 18-24 weeks and 0-6 weeks).

The invention claimed is:

1. A method for treating a human subject suffering from a bone fracture, the method comprising systemically administering to the subject an effective amount of a population of cells enriched for STRO-1$^+$ multipotential cells and/or multipotential progeny thereof to treat the subject's bone fracture and thereby treat the subject.

2. The method of claim 1, wherein the STRO-1$^+$ multipotential cells are STRO-1$^{bright}$ multipotential cells.

3. The method of claim 1, wherein the administered effective amount of cells comprises a number of STRO-1$^+$ multipotential cells sufficient to stimulate at least a five-fold increase in plasma osteocalcin levels within two weeks of administration.

4. The method of claim 3, wherein administration of the population of cells stimulates at least a ten-fold increase in plasma osteocalcin levels within two weeks of administration.

5. The method of claim 1, wherein administration of the population of cells stimulates an increase in plasma alkaline phosphatase levels in the subject.

6. The method of claim 5, wherein administration of the population of cells alone or together with progeny thereof and/or soluble factors derived therefrom results in at least a five percent increase in plasma alkaline phosphatase levels within 6 weeks of administration compared to the level of plasma alkaline phosphatase prior to administration.

7. The method of claim 5, wherein administration of the population of cells alone or together with progeny thereof and/or soluble factors derived therefrom results in at least a ten percent increase in plasma alkaline phosphatase levels within 6 weeks of administration compared to the level of plasma alkaline phosphatase prior to administration.

8. The method of claim 1, wherein the population of cells is administered once every twelve or more weeks.

9. The method of claim 1, comprising administering between $0.1 \times 10^6$ to $5 \times 10^6$ STRO-1$^+$ multipotential cells and/or progeny thereof per kg body weight of the subject.

10. The method of claim 1, comprising administering between $0.3 \times 10^6$ to $2 \times 10^6$ multipotential STRO-1$^+$ cells and/or progeny thereof per kg body weight of the subject.

11. The method of claim 1, wherein the population of cells is administered intravenously.

12. The method of claim 1, wherein the population of cells was culture-expanded prior to the administration.

* * * * *